(12) United States Patent
Miller

(10) Patent No.: US 10,028,973 B2
(45) Date of Patent: Jul. 24, 2018

(54) USING DNA METHYLTRANSFERASE INHIBITORS TO TREAT CALCIFIC AORTA VALVE DISEASE

(71) Applicant: Mayo Foundation for Medical Education and Research, Rochester, MN (US)

(72) Inventor: Jordan D. Miller, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 14/861,428

(22) Filed: Sep. 22, 2015

(65) Prior Publication Data

US 2016/0082025 A1 Mar. 24, 2016

Related U.S. Application Data

(60) Provisional application No. 62/053,406, filed on Sep. 22, 2014.

(51) Int. Cl.
*A61K 31/706* (2006.01)
(52) U.S. Cl.
CPC .................. *A61K 31/706* (2013.01)
(58) Field of Classification Search
CPC .................................................. A61K 31/706
See application file for complete search history.

(56) References Cited

FOREIGN PATENT DOCUMENTS

| EP | 2594270 | 5/2013 |
|----|---------|--------|
| WO | WO2005011727 | 2/2005 |

OTHER PUBLICATIONS

Azechi et al., Journal of Atherosclerosis and Thrombosis, 2014, 21(5), p. 463-476, published online: Jan. 20, 2014.*
Nagy et al., FEBS Letters, 2012, 586, p. 1325-1329.*
Hagemann et al., PLoS One, 2011, 6(3), e17388, p. 1-11.*
Nagy, E., Molecular Mechanisms of Inflammation and Calcification in Aortic Valve Stenosis, Thesis, Karolinska Institutet, Stockholm, Sweden, 2012.*
Acharyya et al., "TNF inhibits Notch-1 in skeletal muscle cells by Ezh2 and DNA methylation mediated repression: implications in Duchenne muscular dystrophy," *PLoS One*, 5(8):e12479, Aug. 30, 2010.
Agrelo, "A new molecular model of cellular aging based on Werner syndrome," *Med Hypotheses*, 68(4):770-780, Epub Oct. 27, 2006.
Amato et al., "Treatment decision in asymptomatic aortic valve stenosis: role of exercise testing," *Heart*, 86(4):381-386, Oct. 2001.
Ballman et al., "Faster cyclic loess: normalizing RNA arrays via linear models," *Bioinformatics.*, 20(16):2778-2786, Epub May 27, 2004.
Barrick et al., "Reduced EGFR causes abnormal valvular differentiation leading to calcific aortic stenosis and left ventricular hypertrophy in C57BL/6J but not 129S1/SvImJ mice," *Am J Physiol Heart Circ Physiol.*, 297(1):H65-H75, Epub May 15, 2009.
Benjamini et al., "Controlling the false discovery rate: a practical and powerful approach to multiple testing," *J Roy Stat Soc B.*, 57(1):289-300, 1995.
Bernstein et al., "The mammalian epigenome," *Cell*, 128(4):669-681, Feb. 23, 2007.
Berry et al., "Biventricular adaptation to vol. overload in mice with aortic regurgitation," *J Cardiovasc Magn Reson.*, 11:27, Aug. 11, 2009.
Bocklandt et al., "Epigenetic predictor of age," *PLoS One.*, 6(6):e14821, Epub Jun. 22, 2011.
Bonow et al., "2008 Focused update incorporated into the ACC/AHA 2006 guidelines for the management of patients with valvular heart disease: a report of the American College of Cardiology/American Heart Association Task Force on Practice Guidelines (Writing Committee to Revise the 1998 Guidelines for the Management of Patients With Valvular Heart Disease): endorsed by the Society of Cardiovascular Anesthesiologists, Society for Cardiovascular Angiography and Interventions, and Society of Thoracic Surgeons," *Circulation*, 118(15):e523-e661, Epub Sep. 26, 2008.
Briand et al., "Metabolic syndrome negatively influences disease progression and prognosis in aortic stenosis," *J Am Coll Cardiol.*, 47(11):2229-2236, Epub May 15, 2006.
Casillas et al., "Transcriptional control of the DNA methyltransferases is altered in aging and neoplastically-transformed human fibroblasts," *Mol Cell Biochem.*, 252(1-2):33-43, Oct. 2003.
Cortazar et al., "Embryonic lethal phenotype reveals a function of TDG in maintaining epigenetic stability," *Nature.*, 470(7334):419-423, Epub Jan. 30, 2011.
Cyr and Domann, "The redox basis of epigenetic modifications: from mechanisms to functional consequences," *Antioxid Redox Signal.*, 15(2):551-589, Epub Feb. 5, 2011.
Dodge et al., "Inactivation of Dnmt3b in mouse embryonic fibroblasts results in DNA hypomethylation, chromosomal instability, and spontaneous immortalization," *J Biol Chem.*, 280(18):17986-17991, Epub Mar. 8, 2005.
Dudoit et al., "Statistical methods for identifying differentially expressed genes in replicated cDNA microarray experiments," *Statistica sinica.*, 12:111-139, Jan. 2002.
Dweck et al., "Calcific aortic stenosis: a disease of the valve and the myocardium," *J Am Coll Cardiol.*, 60(19):1854-1863, Epub Oct. 10, 2012.
Eckel et al., "Normalization of two-channel microarray experiments: a semiparametric approach," *Bioinformatics.*, 21(7):1078-1083, Epub Oct. 28, 2004.
Ellison et al., "Evidence of genetic locus heterogeneity for familial bicuspid aortic valve," *J Surg Res.*, 142(1):28-31, Sep. 2007.

(Continued)

*Primary Examiner* — Jonathan S Lau

(74) *Attorney, Agent, or Firm* — Fish & Richardson P.C.

(57) ABSTRACT

Materials and methods for using DNA methyltransferase inhibitors to slow progression of aortic valve calcification and stenosis are provided.

5 Claims, 17 Drawing Sheets

(56) References Cited

OTHER PUBLICATIONS

Fan et al., "MTSS1, a novel target of DNA methyltransferase 3B, functions as a tumor suppressor in hepatocellular carcinoma," *Oncogene.*, 31(18):2298-2308, Epub Sep. 12, 2011.

Fitzpatrick et al., "Endochondral bone formation in the heart: a possible mechanism of coronary calcification," *Endocrinology.*, 144(6):2214-2219, Jun. 2003.

Garg et al., "Mutations in NOTCH1 cause aortic valve disease,"*Nature*, 437(7056):270-274, Epub Jul. 17, 2005.

Garg, "Molecular genetics of aortic valve disease," *Curr Opin Cardiol.*, 21(3):180-184, May 2006.

Gentleman et al., "Bioconductor: open software development for computational biology and bioinformatics," *Genome Biol.*, 5(10):R80, Epub Sep. 15, 2004.

Golubnitschaja, "Cell cycle checkpoints: the role and evaluation for early diagnosis of senescence, cardiovascular, cancer, and neurodegenerative diseases," *Amino Acids.*, 32(3):359-371, Epub Nov. 30, 2006.

Halaschek-Wiener et al., "Genetic variation in healthy oldest-old," *PLoS One*, 4(8):e6641, Aug. 14, 2009.

He et al., "Regulation and function of DNA methylation in plants and animals," *Cell Res.*, 21(3):442-465, Epub Feb. 15, 2011.

Hinton et al., "Mouse heart valve structure and function: echocardiographic and morphometric analyses from the fetus through the aged adult," *Am J Physiol Heart Circ Physiol.*, 294(6):H2480-H2488, Epub Apr. 4, 2008.

Irizarry et al., "Exploration, normalization, and summaries of high density oligonucleotide array probe level data," *Biostatistics.*, 4(2):249-264, Apr. 2003.

Jurkowska et al., "Structure and function of mammalian DNA methyltransferases," *Chembiochem.*, 12(2):206-222, Epub Nov. 29, 2010.

Khorasanizadeh, "The nucleosome: from genomic organization to genomic regulation," *Cell*, 116(2):259-272, Jan. 23, 2004.

Klein et al., "Mutations in DNMT1 cause hereditary sensory neuropathy with dementia and hearing loss," *Nat Genet.*, 43(6):595-600, Epub May 1, 2011.

Li et al., "DNA methylation, genomic imprinting, and mammalian development," *Cold Spring Harb Symp Quant Biol.*, 58:297-305, 1993.

Li et al., "Synergistic function of DNA methyltransferases Dnmt3a and Dnmt3b in the methylation of Oct4 and Nanog," *Mol Cell Biol.*, 27(24):8748-8759, Epub Oct. 15, 2007.

Li et al., "Targeted mutation of the DNA methyltransferase gene results in embryonic lethality," *Cell*, 69(6):915-926, Jun. 12, 1992.

Lopatina et al., "Differential maintenance and de novo methylating activity by three DNA methyltransferases in aging and immortalized fibroblasts," *J Cell Biochem.*, 84(2):324-334, 2002.

Matsumoto et al., "Regular exercise training prevents aortic valve disease in low-density lipoprotein-receptor-deficient mice," *Circulation*, 121(6):759-767, Epub Feb. 1, 2010.

McKellar et al., "Novel NOTCH1 mutations in patients with bicuspid aortic valve disease and thoracic aortic aneurysms," *J Thorac Cardiovasc Surg.*, 134(2):290-296, Aug. 2007.

Miller et al., "Calcific aortic valve stenosis: methods, models, and mechanisms," *Circ Res.*, 108(11):1392-1412, May 27, 2011.

Miller et al., "Dysregulation of antioxidant mechanisms contributes to increased oxidative stress in calcific aortic valvular stenosis in humans," *J Am Coll Cardiol.*, 52(10):843-850, Sep. 2, 2008.

Miller et al., "Evidence for active regulation of pro-osteogenic signaling in advanced aortic valve disease," *Arterioscler Thromb Vasc Biol.*, 30(12):2482-2486, Epub Sep. 23, 2010.

Miller et al., "Lowering plasma cholesterol levels halts progression of aortic valve disease in mice," *Circulation*, 119(20):2693-2701, Epub May 11, 2009.

Miller et al., "MnSOD protects against COX1-mediated endothelial dysfunction in chronic heart failure," *Am J Physiol Heart Circ Physiol.*, 298(5):H1600-H1607, Epub Mar. 19, 2010.

Ngo et al., "Determinants of occurrence of aortic sclerosis in an aging population," *JACC Cardiovasc Imaging.*, 2(8):919-927, Aug. 2009.

Nigam et al., "Notch1 represses osteogenic pathways in aortic valve cells," *J Mol Cell Cardiol.*, 47(6):828-834, Epub Aug. 18, 2009.

Nkomo et al., "Burden of valvular heart diseases: a population-based study," *Lancet*, 368(9540):1005-1011, Sep. 16, 2006.

Nossaman et al., "Stimulators and activators of soluble guanylate cyclase: review and potential therapeutic indications," *Crit Care Res Pract.*, vol. 2012, Article ID 290805, 12 pages, Epub Feb. 28, 2012.

Nwachukwu et al "Evidence for altered DNA methylation as a major regulator of gene expression in calcific aortic valve disease (671.15)," *The FASEB Journal*, 28(1 Supplement), Apr. 2014.

Nwachukwu et al., "Evidence for altered DNA methylation as a major regulator of gene expression in calcific aortic valve disease," Apr. 2014, 1 page [poster].

Ohtani and Dimmeler, "Epigenetic regulation of cardiovascular differentiation," *Cardiovasc Res.*, 90(3):404-412, Epub Mar. 2, 2011.

Okano et al., "DNA methyltransferases Dnmt3a and Dnmt3b are essential for de novo methylation and mammalian development," *Cell*, 99(3):247-257, Oct. 1999.

Otto and Bonow, Eds., "Cellular and Molecular Basis of Calcific Aortic Valve Disease," *Valvular Heart Disease: A Companion to Braunwald's Heart Disease*, 4th edition, 2014, Chapter 3, pp. 30-52.

R Core Team, R: A language and environment for statistical computing, R Foundation for Statistical Computing, 2007.

Rajamannan et al., "Atorvastatin inhibits hypercholesterolemia-induced calcification in the aortic valves via the Lrp5 receptor pathway," *Circulation*, 112(9 Suppl):I229-I234, Aug. 30, 2005.

Rajamannan et al., "Human aortic valve calcification is associated with an osteoblast phenotype,"*Circulation*, 107(17):2181-2184, Epub Apr. 28, 2003.

Rajamannan, "Calcific aortic stenosis: lessons learned from experimental and clinical studies,"*Arterioscler Thromb Vasc Biol.*, 29(2):162-168, Epub Nov. 20, 2008.

Ray et al., "Aging in heterozygous Dnmt1-deficient mice: effects on survival, the DNA methylation genes, and the development of amyloidosis," *J Gerontol A Biol Sci Med Sci.*, 61(2):115-124, Feb. 2006.

Rosenhek et al., "Mild and moderate aortic stenosis. Natural history and risk stratification by echocardiography," *Eur Heart J.*, 25(3):199-205, Feb. 2004.

Rosenhek et al., "Natural history of very severe aortic stenosis," *Circulation*, 121(1):151-156, Epub Dec. 21, 2009.

Sandoval et al., "Validation of a DNA methylation microarray for 450,000 CpG sites in the human genome," *Epigenetics*, 6(6):692-702, Epub Jun. 1, 2011.

Shao et al., "Inflammation and the osteogenic regulation of vascular calcification: a review and perspective," *Hypertension.*, 55(3):579-592, Epub Jan. 25, 2010.

Smith et al., "A role for the Werner syndrome protein in epigenetic inactivation of the pluripotency factor Oct4," *Aging Cell*, 9(4):580-591, Epub May 10, 2010.

Smyth, "Linear models and empirical bayes methods for assessing differential expression in microarray experiments," *Stat Appl Genet Mol Biol.*, 3:Article3, Epub Feb. 12, 2004.

So et al., "DNA methyltransferase controls stem cell aging by regulating BMI1 and EZH2 through microRNAs," *PLoS One*, 6(5):e19503, May 10, 2011.

Stasch et al., "Soluble guanylate cyclase as an emerging therapeutic target in cardiopulmonary disease," *Circulation.*, 123(20):2263-2273, May 24, 2011.

Subramanian et al., "Dietary cholesterol worsens adipose tissue macrophage accumulation and atherosclerosis in obese LDL receptor-deficient mice," *Arterioscler Thromb Vasc Biol.*, 28(4):685-691, Epub Jan. 31, 2008.

Szyf and Detich, "Regulation of the DNA methylation machinery and its role in cellular transformation," *Prog Nucleic Acid Res Mol Biol.*, 69:47-79, 2001.

(56) References Cited

OTHER PUBLICATIONS

Taberlay and Jones, "DNA methylation and cancer," Prog Drug Res 67:1-23, 2011.

Ueda et al., "Roles for Dnmt3b in mammalian development: a mouse model for the ICF syndrome,"*Development*, 133(6):1183-1192, Mar. 2006.

van Eickels et al., "Role of the sGC activator ataciguat sodium (HMR1766) in cardiovascular disease," *BMC Pharmacology*., 7(Suppl 1):S4, Jul. 25, 2007.

Watson et al., "Hypoxia-induced epigenetic modifications are associated with cardiac tissue fibrosis and the development of a myofibroblast-like phenotype," *Hum Mol Genet*., 23(8):2176-2188, Epub Dec. 2, 2013.

Weiss et al., "Calcific aortic valve stenosis in old hypercholesterolemic mice," *Circulation*, 114(19):2065-2069, Epub Oct. 30, 2006.

Xu et al., "Common pathogenic features of atherosclerosis and calcific aortic stenosis: role of transforming growth factor-beta," *Cardiovasc Pathol*., 19(4):236-247, Epub Nov. 26, 2009.

Xu et al., "Identification of potential genes regulated by DNA methyltransferase 3B in a hepatocellular carcinoma cell line by RNA interference and microarray analysis," *Yi Chuan Xue Bao*., 32(11):1115-1127, Nov. 2005.

Yang et al., "Bone morphogenic protein 2 induces Runx2 and osteopontin expression in human aortic valve interstitial cells: role of Smad1 and extracellular signal-regulated kinase 1/2," *J Thorac Cardiovasc Surg*., 138(4):1008-1015, Epub Aug. 6, 2009.

Zhang et al., "Comparison of global DNA methylation profiles in replicative versus premature senescence," *Life Sci*., 83(13-14):475-480, Epub Aug. 5, 2008.

Zhou et al., "Soluble guanylyl cyclase activation by HMR-1766 (ataciguat) in cells exposed to oxidative stress," *Am J Physiol Heart Circ Physiol*., 295(4):H1763-H1771, Epub Aug. 29, 2008.

\* cited by examiner

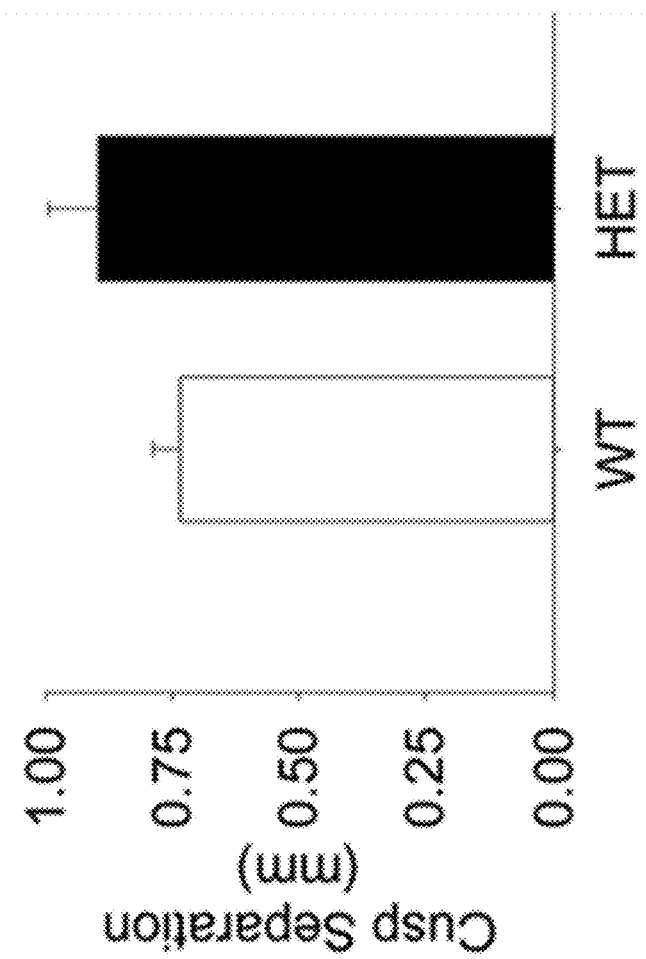

USING DNA METHYLTRANSFERASE INHIBITORS TO TREAT CALCIFIC AORTA VALVE DISEASE

CROSS-REFERENCE TO RELATED APPLICATIONS

This application claims benefit of priority from U.S. Provisional Application Ser. No. 62/053,406, filed Sep. 22, 2014.

STATEMENT AS TO FEDERALLY SPONSORED RESEARCH

This invention was made with government support under HL111121 and HL092235 awarded by the National Institutes of Health. The government has certain rights in the invention.

TECHNICAL FIELD

This document relates to materials and methods for using DNA methyltransferase inhibitors to slow progression of calcific aortic valve disease (CAVD).

BACKGROUND

Aging is associated with progressive increases in cardiovascular calcification (Ngo et al., *JACC Cardiovasc Imaging* 2:919-927, 2009). Hemodynamically significant aortic valve stenosis affects 3% of the population over age 65 (Nkomo et al., *Lancet* 368:1005-1011, 2006), and patients with even moderate aortic valve stenosis (peak velocity of 3-4 m/sec) have a 5 year event-free survival of less than 40% (Amato et al., Heart 86:381-386, 2001; Rosenhek et al., *Circulation* 121:151-156, 2010; Briand et al., *J Am Coll Cardiol* 47:2229-2236, 2006; and Rosenhek et al., *Eur Heart J* 25:199-205, 2004). No treatments have successfully slowed progression of aortic valve calcification, and aortic valve replacement has been the only available treatment for advanced aortic valve stenosis (Bonow et al., *Circulation* 118:e523-661, 2008).

Progression of CAVD appears to be an active process that is fundamentally different from atherosclerosis. Re-differentiation of valvular interstitial cells to an osteoblast-like phenotype may be central to the progression of calcified lesions in stenotic valves (Miller et al., *Arterioscler Thromb Vasc Biol* 30:2482-2486, 2010; Miller et al., *Circulation* 119:2693-2701, 2009; Rajamannan et al., *Circulation* 107:2181-2184, 2003; and Rajamannan, *Arterioscler Thromb Vasc Biol* 29:162-168, 2009), and is strongly associated with increases in bone morphogenetic protein signaling (smad1/5/8 phosphorylation; Miller et al. 2010, supra; Miller et al. 2009, supra; and Yang et al., *J Thorac Cardiovasc Surg* 138:1008-1015, 2009), Wnt/β-catenin signaling (Shao et al., *Hypertension* 55:579-592, 2010; and Rajamannan et al., *Circulation* 112:1229-234, 2005), and transforming growth factor beta signaling (smad2/3 phosphorylation) (Xu et al., *Cardiovasc Pathol* 19:236-247, 2010).

SUMMARY

This document is based at least in part on the discovery that DNA methylation patterns are dramatically altered in patients with calcific aortic valve stenosis (CAVS), and that the changes in DNA methylation are associated with increases in the de novo DNA methyl transferase, DNMT3b. This document also is based at least in part on the notion that increases in DNMT3b suppress protective genes in patients with CAVS, which ultimately is permissive for osteogenic gene expression and promotion of valvular calcification. The materials and methods provided herein can be used to reduce (e.g., slow) the progression of aortic valve calcification.

In one aspect, this document features a method for modulating calcific aortic valve stenosis (CAVS) in a patient. The method can include administering, to a patient identified as having CAVS, a therapeutically effective amount of an inhibitor of a DNA methyltransferase (DNMT) (e.g., an inhibitor of DNA methyltransferase 3b (DNMT3b), an inhibitor of DNA methyltransferase 1 (DNMT1), or an inhibitor of DNA methyltransferase 3a (DNMT3a). The DNMT inhibitor can be 5-aza-2'-deoxycytidine. The method can include administering the DNMT inhibitor in an amount effective to slow progression of CAVS in the patient. The patient can be a human.

In another aspect, this document features a method for modulating fibrosis in an aortic valve of a patient diagnosed with CAVD. The method can include administering to the patient a therapeutically effective amount of a composition comprising a DNMT inhibitor (e.g., an inhibitor of DNMT3b, an inhibitor of DNMT1, or an inhibitor of DNMT3a. The DNMT inhibitor can be 5-aza-2'-deoxycytidine. The method can include administering the DNMT inhibitor in an amount effective to slow progression of fibrosis, calcification, or both in the aortic valve of the patient. The patient can be a human.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 14A and 14B are a series of graphs showing the transcriptional and functional consequences of DNMT3 haploinsufficiency in hypercholesterolemic mice. Inactivation of one copy of DNMT3b reduced osteogenic signaling (Msx2 and Spp1, FIG. 14A, left panels), increased antiosteogenic signaling (FABP4 and Smad6; FIG. 14A, right panels), and improved aortic valve function (cusp separation distance, FIG. 14B) in mice fed a Western diet for six months.

DETAILED DESCRIPTION

Figure 1:
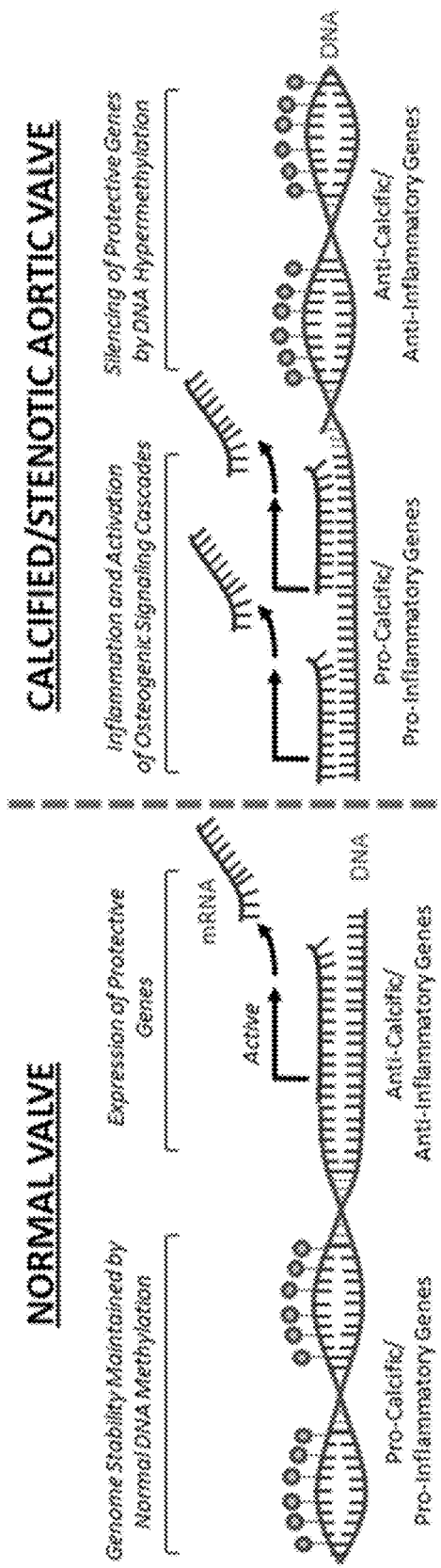
FIG. 1 is a diagram depicting a model of proposed DNA methylation patterns in normal aortic valves (left) and in calcified, stenotic valves (right).

Calcific aortic valve stenosis (CAVS) is the most common form of valve disease in the Western world, but the pathophysiology underlying CAVS is not completely defined. Further, there currently are no effective medical treatments that can alter the course of CAVS, nor are there reliable markers for predicting disease progression.

The pathological processes that occur within the valve during aortic stenosis include inflammation resulting from mechanical stress and endothelial damage that allows infiltration of lipid and inflammatory cells into the valve, fibrosis that occurs when fibroblasts differentiate into myofibroblasts that secrete increased levels of collagen, and calcification driven by microvesicle secretion by macrophages. As described herein, changes in DNA methylation may occur with or affect development and progression of CAVS.

DNA methylation is a critical mechanism for silencing gene expression and maintenance of genome stability (Khorasanizadeh, *Cell* 116:259-272, 2004; Bernstein et al., *Cell* 128:669-681, 2007; Ueda et al., *Development* 133: 1183-1192, 2006; Dodge et al., *J Biol Chem* 280:17986-17991, 2005; Okano et al., *Cell* 99:247-257, 1999; Li et al., *Cold Spring Harb Symp Quant Biol* 58:297-305, 1993; Li et al., *Cell* 69:915-926, 1992; and Cortazar et al., *Nature* 470:419-423, 2011). Methylation of DNA is mediated primarily by three DNA methyltransferase isoforms: DNMT1, DNMT3a, and DNMT3b (He et al., *Cell Res* 21:442-465, 2011; Ohtani and Dimmeler, *Cardiovasc Res* 90:404-412, 2011; and Jurkowska et al., *Chembiochem* 12:206-222, 2011). All three isoforms have been shown to play significant roles in development, but DNMT1 (Ray et al., *J Gerontol A Biol Sci Med Sci* 61:115-124, 2006; Casillas et al., *Mol Cell Biochem* 252:33-43, 2003; Zhang et al., *Life Sci* 83:475-480, 2008; and So et al., *PLoS One* 6:e19503, 2011) and DNMT3b (Smith et al., *Aging Cell* 9:580-591, 2010; Agrelo, *Med Hypotheses* 68:770-780, 2007; Lopatina et al., *J Cell Biochem* 84:324-334, 2002; and Halaschek-Wiener et al., *PLoS One* 4:e6641, 2009) appear to play the greatest roles in altering DNA methylation with aging and age-related diseases.

With normal aging, "global" DNA methylation is progressively reduced due to progressive reductions in DNMT1 expression and activity (Ray et al. supra; Zhang et al. supra; Bocklandt et al., *PLoS One* 6:e14821, 2011; and Cyr and Domann, *Antioxid Redox Signal* 15:551-589, 2011), which contributes to genomic instability and aberrant gene expression (Klein et al., *Nat Genet* 43:595-600, 2011; Golubnitschaja, *Amino Acids* 32:359-371, 2007; and Szyf and Detich, *Prog Nucleic Acid Res Mol Biol* 69:47-79, 2001).

DNMT1-haploinsufficient mice have an increased incidence of amyloidosis, but do not exhibit shortened lifespans or increased susceptibility to other age-related diseases (Ray et al. supra). Interestingly, the data presented herein suggest that global DNA methylation is increased in CAVD despite reductions in DNMT1 expression.

In response to aging, inflammation, or other exogenous stressors, de novo epigenetic marks placed on DNA are most often the consequence of increases in DNMT3b (Smith et al. supra; and Acharyya et al., *PLoS One* 5:e12479, 2010). Important DNMT3b methylation targets include promoters of tumor suppressor genes, genes regulating cellular multi-potency, and genes known to suppress osteogenic signaling (Fan et al., *Oncogene* 31:2298-2308, 2011; Taberlay and Jones, *Prog Drug Res* 67:1-2, 2011; Smith et al. supra; Szyf and Detich supra; Acharyya et al. supra; Li et al., *Mol Cell Biol* 27:8748-8759, 2007; and Xu et al., *Yi Chuan Xue Bao* 32:1115-1127, 2005). The data presented herein suggest that DNMT3b expression is significantly increased in valve tissue from humans with CAVD.

DNMT3b may play a key regulatory role in osteogenic re-differentiation in CAVD. Studies have demonstrated that treatment of skeletal myoblasts with TNFα elicits increases in DNMT3b expression and activity, which results in repression of Notch1 expression due to hypermethylation of its promoter (Acharyya et al. supra). Mutations in Notch1 contribute to bicuspid valve formation and valve calcification in humans (Ellison et al., *J Surg Res* 142:28-31, 2007; McKellar et al., *J Thorac Cardiovasc Surg* 134:290-296, 2007; Garg, *Curr Opin Cardiol* 21:180-184, 2006; and Garg et al., *Nature* 437:270-274, 2005), and Notch1 inhibits osteogenic signaling in interstitial cells from tricuspid valves in vitro and in vivo in mice (Nigam et al., *J Mol Cell Cardiol* 47:828-834, 2009).

In addition, DNMT3b is an important regulator of cellular multi-potency (Szyf and Detich, supra; Li et al. supra; and Xu et al. supra), and may play a role in determining the susceptibility of valvular interstitial cells to acquire an osteoblast-like phenotype. Specifically, DNMT3b can hypermethylate and suppress Oct4 expression (Smith et al. supra; and Li et al. supra), which may increase the multi-potency of aortic valve interstitial cells and be an initial permissive event allowing for osteogenic differentiation in CAVD.

As indicated in FIG. 1, increases in DNMT3b due to aging, hypercholesterolemia, and inflammation may contribute to repression of anti-calcific genes in CAVD, possibly in a cell-type specific manner as discussed in the Examples below. The context dependence of DNMT3b ultimately may make it a key orchestrator of cellular differentiation and valvular calcification in CAVD.

This document provides methods for treating a subject to reduce or slow aortic valve calcification, fibrosis, and/or stenosis, thus slowing progression of CAVD in the subject. The subject can be, for example, a human patient diagnosed with CAVD. In some cases, the subject can be a research animal (e.g., a mouse, rat, rabbit, dog, pig, sheep, or monkey).

The methods of treatment provided herein can be performed in a variety of suitable manners.

In some embodiments, for example, a method for chronic treatment can include administration of a low dose (e.g., 1 ng/kg/day to 10 mg/kg/day, such as 5 ng/kg/day, 10 ng/kg/day, 50 ng/kg/day, 100 ng/kg/day, 500 ng/kg/day, 1 µg/kg/day, 5 µg/kg/day, 10 µg/kg/day, 50 µg/kg/day, 100 µg/kg/day, 500 µg/kg/day, 1 mg/kg/day, 2.5 mg/kg/day, or 5 mg/kg/day) of a DNMT inhibitor for an extended length of time (e.g., one week or more, two weeks or more, or four weeks or more), or administration of an inhibitor of a specific DNMT (e.g., DNMT1, DNMT3a, or DNMT3b). The methods provided herein can reduce DNA methylation to such an extent that anti-osteogenic/protective genes are no longer repressed by hypermethylation, and thus can allow for re-activation of anti-osteogenic/protective genes that subsequently can slow progression of valve calcification.

In some embodiments, the methods provided herein can include intermittent treatment with a DNMT3b inhibitor. Such approaches can include administration of a relatively high dose (e.g., 10 mg/kg/day to 1 g/kg/day, such as 25 mg/kg/day, 50 mg/kg/day, 100 mg/kg/day, 250 mg/kg/day, 500 mg/kg/day, or 750 mg/kg/day) of DNMT inhibitor for a short period of time (e.g., 0.5 day, one day, two days, three days, four days, 5 days, 6 days, or 7 days), which may result in a substantial reduction in DNA methylation. Such methods also may include a period of "recovery" that can prevent deleterious/unwanted side effects secondary to chronic treatment with DNMT inhibitors.

In some embodiments, the methods provided herein can include chronic treatment with compounds that can activate or de-repress enzymes that demethylate DNA (e.g., the TET1/2 genes). Such methods also may include acute or chronic treatment with low-dose decitabine alone (as TET2 can be repressed by DNA hypermethylation), or can include co-administration of a DNMT inhibitor in combination with one or more activators of EGR4 or Sox5 (which are known to bind to the TET2 promoter and drive expression).

One or more DNMT inhibitors can be incorporated into a composition for administration to a mammal (e.g., a research animal or a human patient diagnosed as having CAVD). For example, DNMT inhibitor as described herein can be administered to a mammal (e.g., a human) under conditions wherein the progression of fibrosis, calcification, and stenosis of the mammal's aortic valve is reduced in a therapeutic manner. Compositions containing one or more DNMT inhibitors can be given once or more daily, weekly, monthly, or even less often, or can be administered continuously for a period of time (e.g., hours, days, or weeks). In some cases, preparations can be designed to stabilize such DNMT compounds and maintain effective activity in a mammal for several days.

The DNMT inhibitor(s) to be administered to a mammal can be admixed, encapsulated, conjugated or otherwise associated with other molecules, molecular structures, or mixtures of compounds such as, for example, liposomes, receptor or cell targeted molecules, or oral, topical or other formulations for assisting in uptake, distribution and/or absorption. In some cases, a composition to be administered can contain one or more DNMT inhibitors in combination with a pharmaceutically acceptable carrier. Pharmaceutically acceptable carriers include, for example, pharmaceutically acceptable solvents, suspending agents, or any other pharmacologically inert vehicles for delivering compounds to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water, saline solution, binding agents (e.g., polyvinylpyrrolidone or hydroxypropyl methylcellulose); fillers (e.g., lactose or dextrose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate).

Acceptable solvents for delivery of DNMT inhibitors can include, without limitation, common physiological salt solutions such as 0.9% sodium chloride, or isotonic aqueous solutions of sodium phosphate buffered to a pH of 7.4.

Pharmaceutical compositions containing one or more DNMT inhibitors as described herein can be administered by a number of methods, including oral, subcutaneous, intrathecal, intraventricular, intramuscular, intraperitoneal, or intravenous injection, or elution from implanted devices/structures.

Exemplary DNMT inhibitors that can be used in the methods and compositions provided herein include, without limitation, those listed in the following paragraphs. Other inhibitors can be identified by, for example, screening libraries of compounds such as small molecules for the ability to inhibit DNMT activity. By comparing the ability of compounds to inhibit the activity of DNMT3b to its ability to inhibit the activity of other DNMTs (e.g., DNMT1 and/or DNMT3a), selective DNMT3b inhibitors can be identified.

Decitabine (5-Aza-2'-deoxycytidine; DAC): An epigenetic modifier that inhibits DNA methyltransferase activity which results in DNA demethylation (hypomethylation) and activation of gene expression by remodeling allowing transcription factor binding.

Genes are synergistically reactivated when demethylation is combined with histone hyperacetylation. The structure of decitabine is:

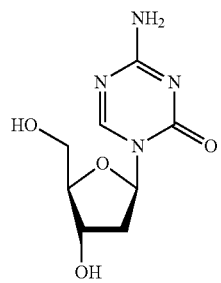 [SMILES: Nc1ncn([C@H]2C[C@@H](O)[C@@H](CO)O2)c(=O)n1]

5-Azacytidine: A potent growth inhibitor and cytotoxic agent; inhibits DNA methyltransferase, an important regulatory mechanism of gene expression, gene activation and silencing. Causes DNA demethylation or hemi-demethylation, creating openings that allow transcription factors to bind to DNA and reactivate tumor suppressor genes. The structure of 5-Azacytidine is:

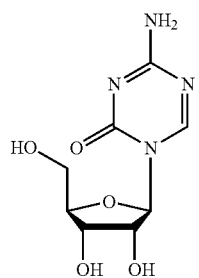

Zebularine: A cytidine analogue, cytidine deaminase inhibitor, and DNA demethylating agent. The structure of zebularine is:

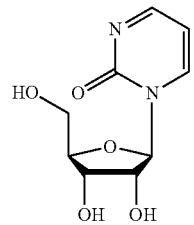

Caffeic acid: A natural dietary phenolic compound found in plants that is an anti-oxidant. Inhibits the synthesis of leukotrienes that are involved in immunoregulation, inflammation and allergy. Inhibits Cu2+-induced LDL oxidation. The structure of caffeic acid is:

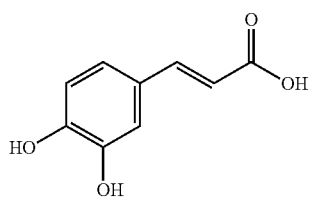 [SMILES: O=C(O)/C=C/c1ccc(O)c(O)c1]

Chlorogenic acid: A natural compound that is the ester of caffeic acid and (−)-quinic acid. Chlorogenic acid is known as an antioxidant, and is an important intermediate in lignin biosynthesis. The structure of chlorogenic acid is:

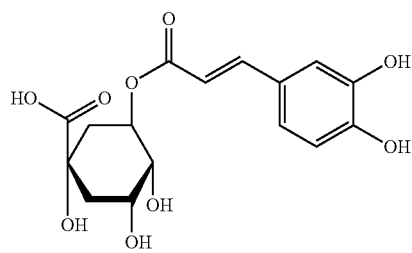

Epigallocatechin gallate (EGCG): Antioxidant polyphenol flavonoid that inhibits telomerase and DNA methyltransferase. EGCG blocks the activation of EGF receptors and HER-2 receptors. ECGG inhibits fatty acid synthase and glutamate dehydrogenase activity. The structure of EGCG is:

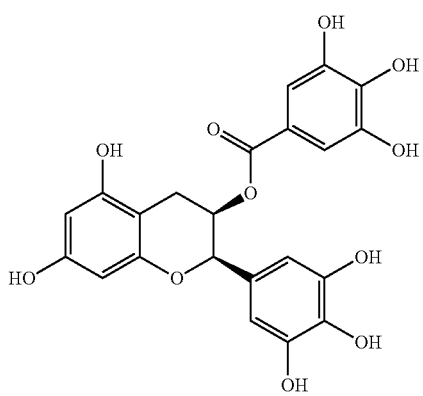 [SMILES: O=C(O[C@@H]1Cc2c(O)cc(O)cc2O[C@@H]1c1cc(O)c(O)c(O)c1)c1cc(O)c(O)c(O)c1]

Hydrazine hydrochloride: Inhibits DNA methyltransferase and modulates epigenetic regulation of gene expression. Non-selective MAO-AB inhibitor; antihypertensive; semicarbazide-sensitive amine oxidase inhibitor. The structure of hydrazine hydrochloride is:

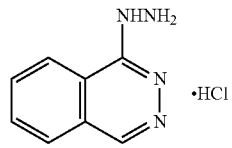 [SMILES: NNc1nncc2ccccc12 ; Cl]

Procainamide hydrochloride: Inhibits DNA methyltransferase and modulates epigenetic regulation of gene expression. $Na^+$ channel blocker and Class IA anti-arrhythmic. The structure of procainamide hydrochloride is:

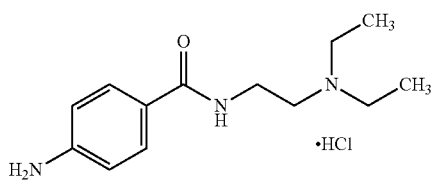 [SMILES: CCN(CC)CCNC(=O)c1ccc(N)cc1 ; Cl]

Pyrocaine hydrochloride: $Na^+$ channel blocker with the structure:

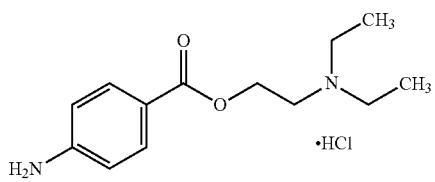 [SMILES: CCN(CC)CCOC(=O)c1ccc(N)cc1 ; Cl]

RG108: Reactivates tumor suppressor gene expression (p16, SFRP1, secreted frizzled related protein-1, and TIMP-3) in tumor cells by DNA demethylation. RG108 also inhibits human tumor cell line (HCT116, NALM-6) proliferation and increased doubling time in culture. The structure of RG108 is:

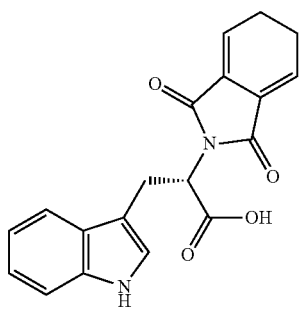 [SMILES: O=C(O)[C@H](Cc1c[nH]c2ccccc12)N1C(=O)C2=CCCC=C2C1=O]

Thioguanine: Ribosylated and phosphorylated by the same pathway as natural purine bases; as the nucleotide, inhibits a variety of cellular processes involved in nucleic acid synthesis. The structure of thioguanine is:

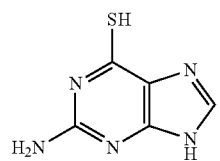 [SMILES: Nc1nc(S)c2nc[nH]c2n1]

SGI-110: DNA hypomethylating agent with the following structure:

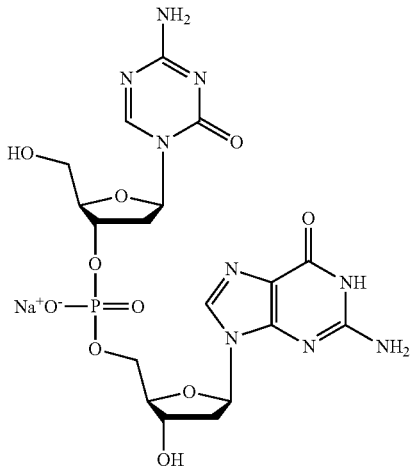

SGI-1027: Quinoline derivative (N-(4-(2-amino-6-methylpyrimidin-4-ylamino)phenyl)-4-(quinolin-4-ylamino)benzamide); a potent inhibitor of DNMT1, DNMT3A, and DNMT3B. The structure of SGI-1027 is:

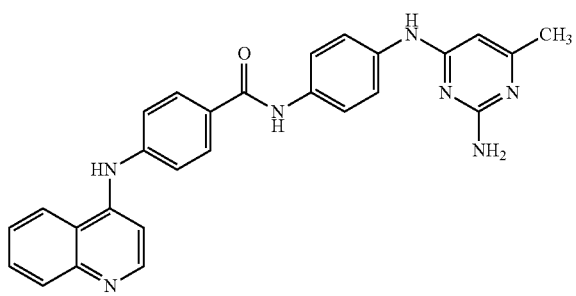 [SMILES: Cc1cc(Nc2ccc(NC(=O)c3ccc(Nc4ccnc5ccccc45)cc3)cc2)nc(N)n1]

The invention will be further described in the following examples, which do not limit the scope of the invention described in the claims.

EXAMPLES

Example 1

Figure 2:
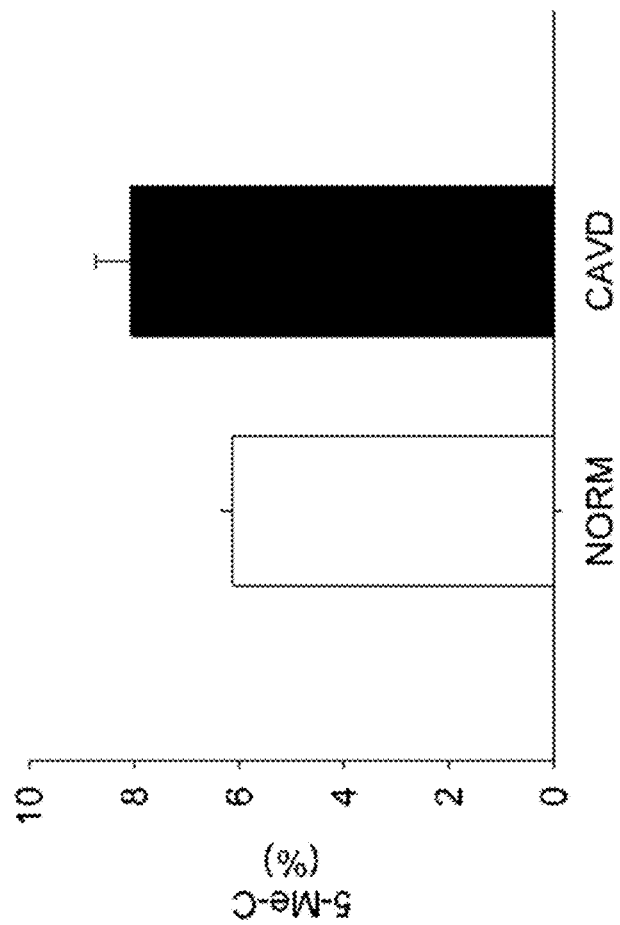
FIG. 2 is a graph plotting global DNA methylation in normal and stenotic human aortic valve tissue, assayed from bisulfite-converted DNA samples isolated from normal and stenotic human valves, using an ELISA-based assay.

Evaluation of Total DNA Methylation, Methylation Patterns, and Expression of Genes (e.g., DNMT3b) in Valve Tissue from Normal Humans and Humans with Severe Calcific Aortic Valve Stenosis To determine whether total genomic DNA methylation is altered valve tissue from humans with CAVD, global DNA methylation was measured in aortic valves from patients with and without calcific aortic valve stenosis, a quantitative fluorometric assay (Epigentek). These experiments demonstrated that total DNA methylation was increased in valve tissue from patients with CAVD (FIG. 2). This differed fundamentally from observations in atherosclerosis, where DNA methylation is reduced.

Figure 3:
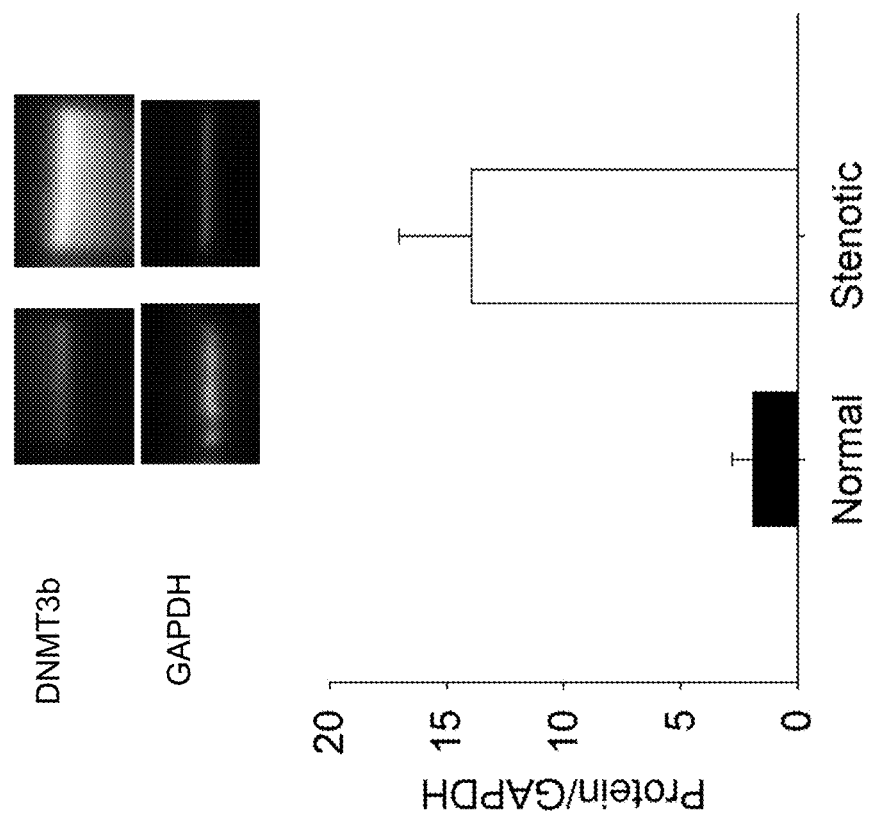
FIG. 3 contains pictures (top portion) of selected sections of a Western blot, showing that DNA methyltransferase 3b (DNMT3b) protein levels are increased in valve tissue from humans with end-stage CAVD. Non-stenotic/normal and stenotic human aortic valve tissue was snap-frozen, pulverized, and processed in protein lysis buffer before Western blotting analysis. The bottom panel of FIG. 3 contains a graph plotting DNMT3b protein levels in the normal and stenotic tissue, as normalized to GAPDH levels in the tissues.

DNMT isoform expression also was measured in aortic valves from patients with and without calcific aortic valve stenosis, demonstrating that DNMT3b was the only DNA methyltransferase isoform increased in aortic valve tissue from patients with CAVD (FIG. 3). Activity of DNMT1, DNMT3a, and DNMT3b also is measured in cells from cultured valve interstitial cells from human or mouse aortic valves using a commercially available DNMT activity assay (Epigentek).

For high throughput determination of whether DNA methylation patterns are altered in valve tissue from patients with CAVD, experiments were performed to characterize DNA methylation patterns using an Infinium 450k Beadchip assay, which measures DNA methylation at more than 450,000 annotated sites (including CpG islands, CpG island "shores", non-CpG methylated sites, and methylation sites located within miRNA promoter regions; Sandoval et al., Epigenetics 6:692-702, 2011). This assay requires 500 ng of bisulfite modified DNA. In brief, samples undergo isothermal whole genome amplification, followed by fragmentation and precipitation. These steps typically yield about 50 µg/reaction and an average size after digestion of ~100-200 bases. Denatured products are hybridized to activated beads using a 5' amino group. The allele specific extension reaction, washing and staining are carried out in a TECAN Te-Flow Chamber. Stained BeadChips are then dried and imaged on an Illumina BeadArray reader. Following scanning on a BeadArray or iScan reader, intensity data are loaded into the GenomeStudio Methylation Module for analysis. Analysis includes control probes for assessing sample-independent and -dependent performance. The methylation status of target cytosines is determined by comparing the ratio of fluorescent signal from the methylated allele to the sum of the fluorescent signal from both methylated and unmethylated alleles. These values range from 0 (unmethylated) to 1 (methylated).

Figure 4:
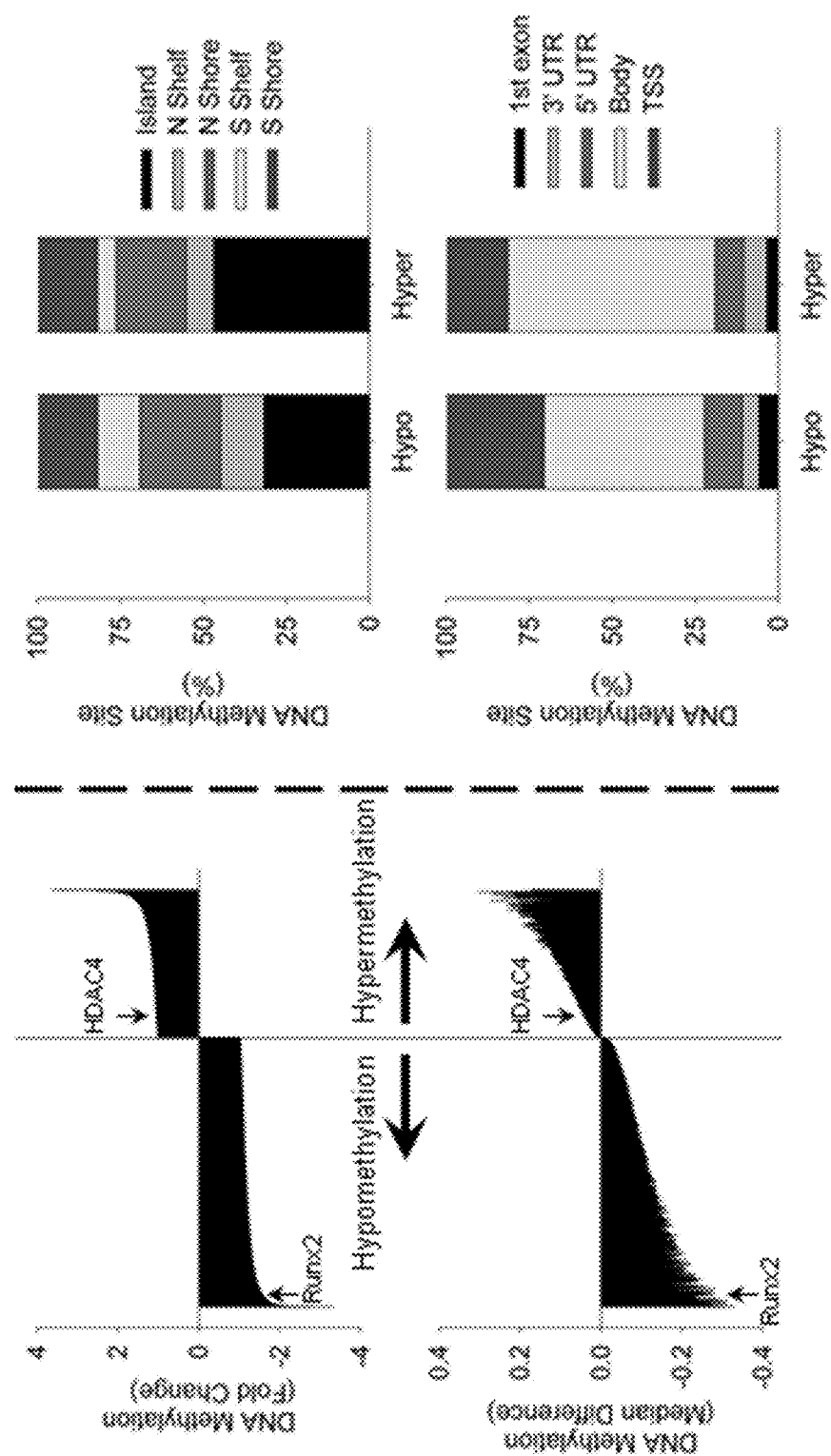
FIG. 4 is a diagram depicting the effects of CAVD on DNA methylation patterns in valve tissue from patients with calcific aortic valve stenosis. The left panels depict changes in methylation of >6000 sites that were significantly changed in CAVS tissue (p<0.05). The right panels depict the location of these sites in relation to the genome and known gene regions (e.g., transcription start sites/TSS).

Ten non-calcified/normal valves and ten valves from patients with CAVD were used in these studies. The analysis revealed that more than 6,000 sites were differentially methylated in valve tissue from patients with CAVD, with the majority of differential DNA methylation occurring in CpG islands and in the body of genes (FIG. 4). Further, the DNA methylation patterns observed in CAVD patients favored activation of osteogenic transcriptional patterns (e.g., hypomethylation of Runx2) and repression of anti-calcific genes (e.g., hypermethylation of HDAC4, a co-repressor of Runx2).

Pyrosequencing of specific genes/methylation sites also are used to confirm, characterize, and quantitate DNA methylation of ten promoter sites with the greatest fold change in methylation levels in stenotic aortic valves (5 of each gene with greatest fold increase or decrease in methylation). Primers are designed using Pyrosequencing Assay Design Software, and 30 ng of DNA is amplified using PCR. The PCR reaction includes one biotinylated primer, allowing for purification of the denatured, single-stranded amplicon with streptavidin-coated beads using a pyrosequencing vacuum workstation. The single-stranded product is annealed to 0.3 µM of the sequencing primer complementary to the single-stranded template, placed at 85° C. for 2 minutes, and cooled to room temperature for 5 minutes. Pyrosequencing reactions are performed on a Biotage Pyro-Mark MD System. Raw data are analyzed using Pyro Q-CpG 1.0.9 analysis software. The degree of each methylation at each CpG position in a sequence is determined from the ratio of T and C.

In addition, subsets of specific genes that are closely related to pro-calcific signaling and osteogenic differentiation also are characterized in these studies. To determine whether changes in methylation are associated with alterations in gene expression, microarrays were used as a non-biased method to identify differentially expressed genes in normal and stenotic aortic valves, and to determine whether differences in gene promoter methylation levels are strong predictors of differential expression in calcific aortic valve disease. Microarray analysis was conducted with an Affymetrix 3' IVT Express kit (Santa Clara, Calif.). Briefly, RNA quality was assessed using an Agilent Bioanalyzer (Santa Clara, Calif.). Reverse transcription to second strand cDNA was generated from 100 ng of total RNA (RIN>7.0). The products were column-purified (Affymetrix) and in vitro transcribed to generate biotin-labeled cRNA. The IVT products were then column-purified, fragmented, and hybridized onto Affymetrix GENECHIPS® at 45° C. for 16 hours (human sample array: U133 Plus 2.0, mouse sample array: 430 2.0). The arrays were washed, stained with streptavidin-phycoerythrin, and scanned in an Affymetrix GENECHIP® Scanner 3000 (Santa Clara, Calif.). All control parameters were confirmed to be within normal ranges before normalization and data reduction were initiated. Twenty genes are selected from the microarray dataset (ten of the most upregulated and ten of the most downregulated) to confirm changes in expression using quantitative real-time RT-PCR. For these studies, tissues from 50 normal and 50 stenotic human aortic valves are ultimately used. Thus far, high-quality RNA (RIN>7.0, 260/280>1.8) has been isolated and microarray analyses have been conducted on tissue from eight human aortic valves (four normal, four stenotic). Beadchip array-quality DNA and protein have been isolated from the same tissue samples (using subfractions of pulverized tissue).

Example 2

Acute and Chronic DNA Methyltransferase Inhibition by Decitabine Treatment of Mice To determine whether acute DNA methyltransferase inhibition promotes anti-calcific gene expression patterns in mice with established calcific aortic valve disease, ldlr$^{-/-}$/apoB$^{100/100}$ (LA) mice were placed on a Western diet for 6 months (which produces mild to moderate valvular dysfunction), and treated with vehicle or Decitabine (5-aza-2'-deoxycytidine; "DAC") for 5 days (0.5 or 1 mg/kg/day, i.p.). Changes in cardiac and aortic valve function at 3 and 6 months are evaluated. Sixty-five mice from each treatment group are sacrificed at the 6 month time point, which represents a stage of mild to moderate CAVD. The first group is used for evaluation of global DNA methylation and methylation of targets identified from human tissue as in Example 1 (n=20), using pyrosequencing. The second group is used for semi-quantitative histological/immunohistochemical evaluation of aortic valve (n=10). The third group is used for genome-wide evaluation of gene expression using microarrays (n=20), and the fourth group is used for high-resolution µCT scanning for quantitation of calcium burden in aortic valve and root (n=15).

Figure 5:
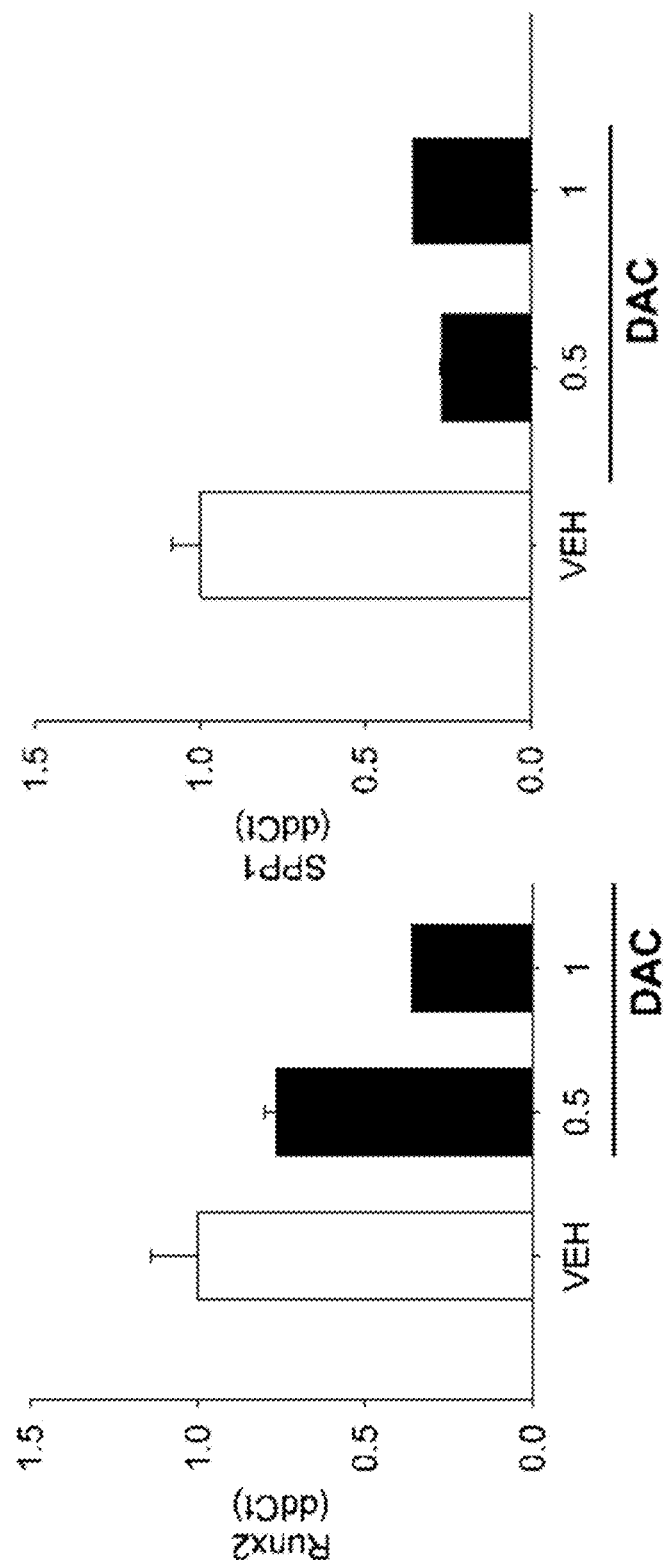
FIG. 5 is a pair of graphs plotting the effects of DNMT inhibition with decitabine (DAC) on expression of the pro-osteogenic signaling genes, Runx2 and osteopontin (SPP1), in mouse aortic valves in vivo. DAC was administered using daily intraperitoneal injections at the doses indicated (mg/kg/day) for 5 days, and gene expression was measured using quantitative real-time RT-PCR and mRNA isolated from mouse aortic valve tissue.
Figure 6:
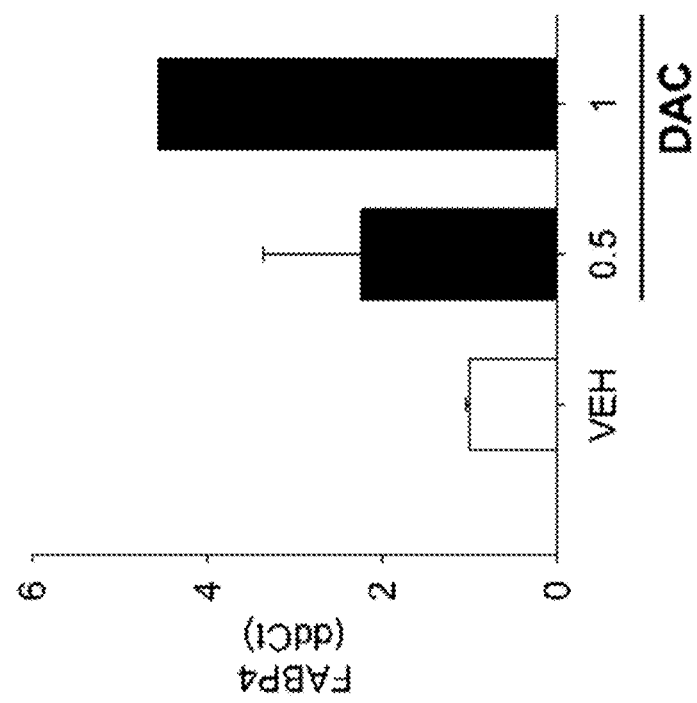
FIG. 6 is a graph plotting the effects of DNMT inhibition with DAC on expression of the anti-osteogenic gene, FABP4 (a PPARγ target). DAC was administered using daily intraperitoneal injections at the doses indicated (mg/kg/day) for 5 days, and gene expression was measured using quantitative real-time RT-PCR and mRNA isolated from mouse aortic valve tissue.
Figure 7:
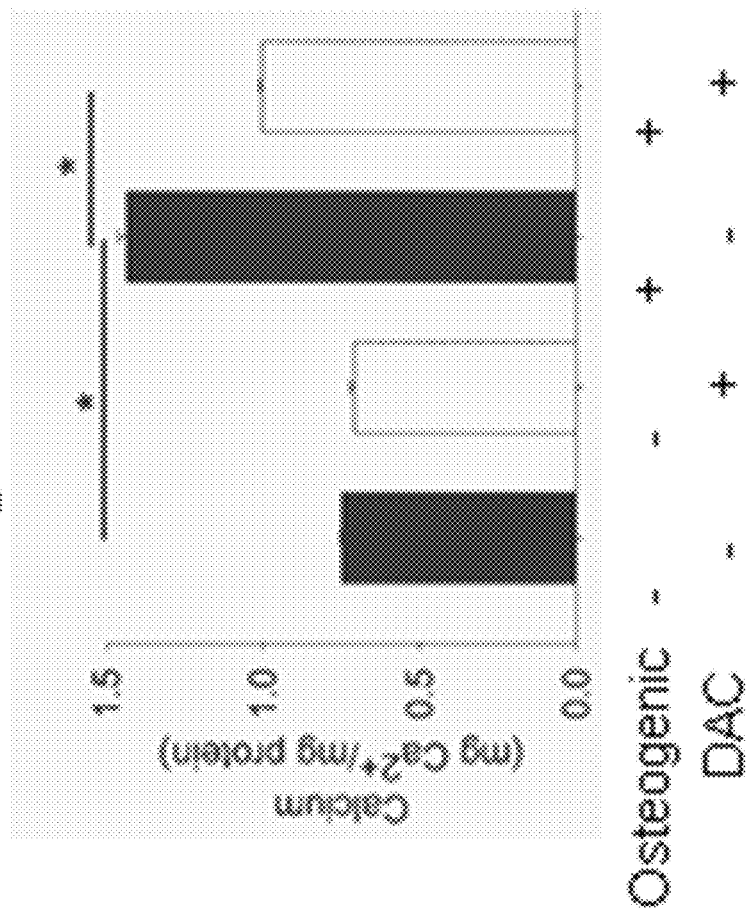
FIG. 7 is a graph plotting the effects of DNMT inhibition with DAC calcium deposition in pig aortic valve interstitial cells in vitro.

These studies demonstrated that inhibition of DNA methyltransferase activity resulted in dose-dependent reductions in Runx2 (FIG. 5) and Sp7 (transcription factors that drive osteogenic differentiation) in mice with established CAVD, and also led to increased PPARγ target gene expression (e.g., FABP4; FIG. 6). PPARγ activation inhibits osteogenic differentiation, and this pattern is consistent with de-repression of anti-calcific gene expression with DNA methyltransferase inhibition. In addition, these experiments showed that inhibition of DNA methyltransferase activity reduced calcification in aortic valve interstitial cells in vitro (FIG. 7).

Figure 8:
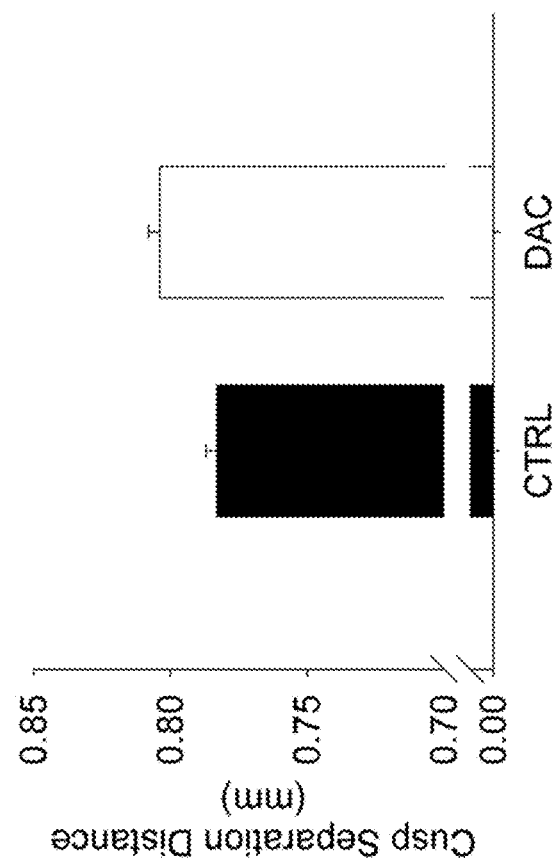
FIG. 8 is a graph plotting cusp separation distance in control mice and in mice treated with DAC (0.1 mg/kg i.p., 2 days/week for 3 months). The reduction of DNA methylation with low-dose DAC slowed progression of aortic valve stenosis in the animals (larger cusp separation distance=improved valve function).

Further studies revealed that treatment of mice with low-dose Decitabine successfully slowed progression of aortic valve calcification and stenosis in hypercholesterolemic mice in vivo (FIG. 8).

Example 3

Targeted Reduction of DNMT3b in Aortic Valve Endothelial Cells or in Aortic Valve Interstitial Cells Reduces Bone Morphogenetic Protein Elaboration and Osteogenic Signaling and Increases Anti-Osteogenic Gene Expression in Mice Mice with targeted reduction of DNMT3b are evaluated for cardiac and aortic valve function, and valves are harvested for histological/immunohistochemical analysis, as well as evaluation of high and low throughput gene expression (microarrays and qRT-PCR), oxidative stress and inflammation, DNMT3b target methylation levels, and μCT scanning at 3, 12, and 18 months of age. The primary comparison is between Tie2-Cre$^-$/DNMT3b$^{FL/FL}$ and Tie2-Cre$^+$/DNMT3b$^{FL/FL}$ littermate-matched mice, or between Pax3-Cre$^-$/DNMT3b$^{FL/FL}$ and Pax3-Cre$^+$/DNMT3b$^{FL/FL}$ littermate-matched mice.

ldlr$^{-/-}$/apoB$^{100/100}$/DNMT3b$^{+/-}$ mice and their ldlr$^{-/-}$/apoB$^{100/100}$/DNMT3b$^{+/+}$, littermate controls are used for these studies. Mice are maintained on a Western diet (TD88137, Harlan Teklad) and housed in a pathogen-free facility, and cardiac and aortic valve function are evaluated at 3, 6, and 9 month time points using echocardiography. Sixty-five mice of each genotype (LA-DNMT3b$^{+/+}$, LA-DNMT3b$^{+/-}$) are sacrificed at 3 and 9 month time points to represent early- and late-stage calcific aortic valve disease, respectively. The first group is used for evaluation of global DNA methylation and methylation of targets identified from human tissue as described in Example 1. Preliminary studies showed that a minimum of 400 ng of DNA can be obtained after pooling aortic valve tissue from two to three mice, providing enough sample to evaluate total DNA methylation (ELISA-based assay, Epigentek) and site-specific DNA methylation of >6 genes using bisulfite-converted DNA followed by pyrosequencing (20 mice of each genotype=7-10 pooled samples). The second group is used for semi-quantitative histological/immunohistochemical evaluation of aortic valve (n=10 per time point). The third group is used for genome-wide evaluation of gene expression using microarrays. Preliminary studies suggested that 20 mice from each genotype are required to obtain adequate high-quality RNA for these studies (pooling of valves from four mice of each genotype=five pooled samples at each time point). The fourth group is used for high-resolution μCT scanning for quantitation of calcium burden in aortic valve and root (n=15 per time point).

Figure 9:
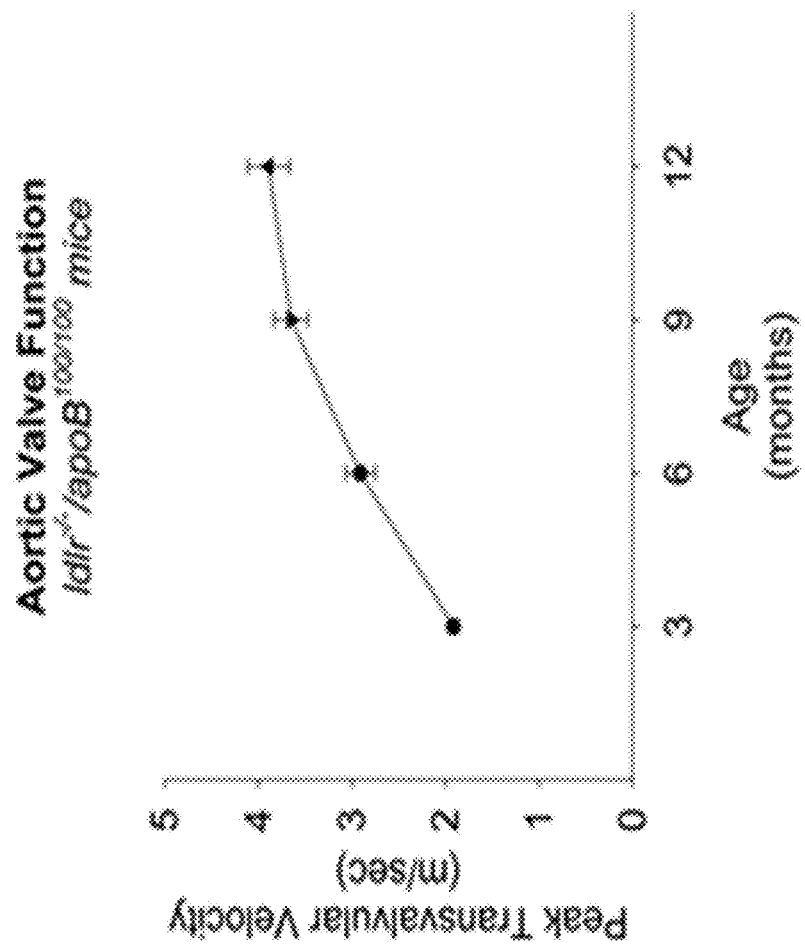
FIG. 9 is a graph plotting changes in aortic valve function in $ldlr^{-/-}/apoB^{100/100}$ mice over time.

Breeding Schemes—Triple Mutation Animals: Valvular calcification and stenosis in ldlr$^{-/-}$/apoB$^{100/100}$ mice has been described (Miller et al. 2010, supra; Miller et al. 2009, supra; and Weiss et al., *Circulation* 114:2065-2069, 2006); characterization of the phenotype of the ldlr$^{-/-}$/apoB$^{100/100}$ colony is shown in FIG. 9 (data are from mice maintained on a Western diet). Mice are generated according to a previously established breeding scheme for the generation of triple-gene manipulation mice. In brief, ldlr$^{-/-}$/apoB$^{100/100}$ mice are crossed with mice carrying an additional manipulated gene of interest (e.g., DNMT3b$^{+/-}$ mice). The offspring are then backcrossed to ldlr$^{-/-}$/apoB$^{100/100}$ mice until they are ldlr$^{-/-}$/apoB$^{100/100}$/DNMT3b$^{+/-}$, which are used as colony founders.

Breeding Schemes—Cell-Type Specific Knockout Mice: DNMT3b-floxed mice (DNMT3b$^{FL/FL}$) are obtained from the Mutant Mouse Regional Resource Center (University of North Carolina at Chapel Hill).

DNMT3b was deleted in valvular endothelial cells by intercrossing DNMT3b$^{FL/FL}$ mice with mice carrying cre recombinase under the control of the Tie2 promoter (Tie2$^{Cre/0}$), to generate DNMT3b$^{FL/+}$/Tie2$^{Cre/0}$ founders. Intercrossing these mice allows for littermate-matching of DNTM3B$^{+/+}$, DNTM3B$^{FL/+}$, and DNTM3B$^{FL/FL}$ mice that express (Tie2$^{Cre/0}$) or do not express (Tie2$^{0/0}$) cre recombinase in endothelial cells. Cre recombinase is expressed in the female germline of Tie2$^{Cre/0}$ mice, but not in the male germline (Fan et al., supra). Consequently, all breeder pairs are set up with DNTM3B$^{FL/+}$/Tie2$^{Cre/0}$ sires and DNTM3B$^{FL/+}$/Tie2$^{0/0}$ dams. Examination of founders and initial offspring generated for these studies showed that the DNTM3B$^{FL/FL}$/Tie2$^{Cre/0}$ mice are viable and grossly normal.

DNTM3B was deleted in neural crest-derived cells by intercrossing DNTM3B$^{FL/FL}$ mice with mice carrying cre recombinase under the control of the Pax3 promoter (Pax3$^{Cre/0}$) to generate DNTM3B$^{FL/+}$/Pax3$^{Cre/0}$ founders. Intercrossing these mice allows for littermate-matching of DNTM3B$^{+/+}$, DNTM3B$^{FL/+}$, and DNTM3B$^{FL/FL}$ mice that carry (Pax3$^{Cre/0}$) or do not carry (Pax3$^{0/0}$) cre recombinase. Breeder pairs are set up with DNTM3B$^{FL/+}$/Pax3$^{Cre/0}$ sires and DNTM3B$^{FL/+}$/Pax3$^{0/0}$ dams. Examination of founders generated for these studies showed that the mice breed well, and that DNTM3B$^{FL/FL}$/Pax3$^{Cre/0}$ mice are viable, fertile, and grossly normal.

Figure 10:
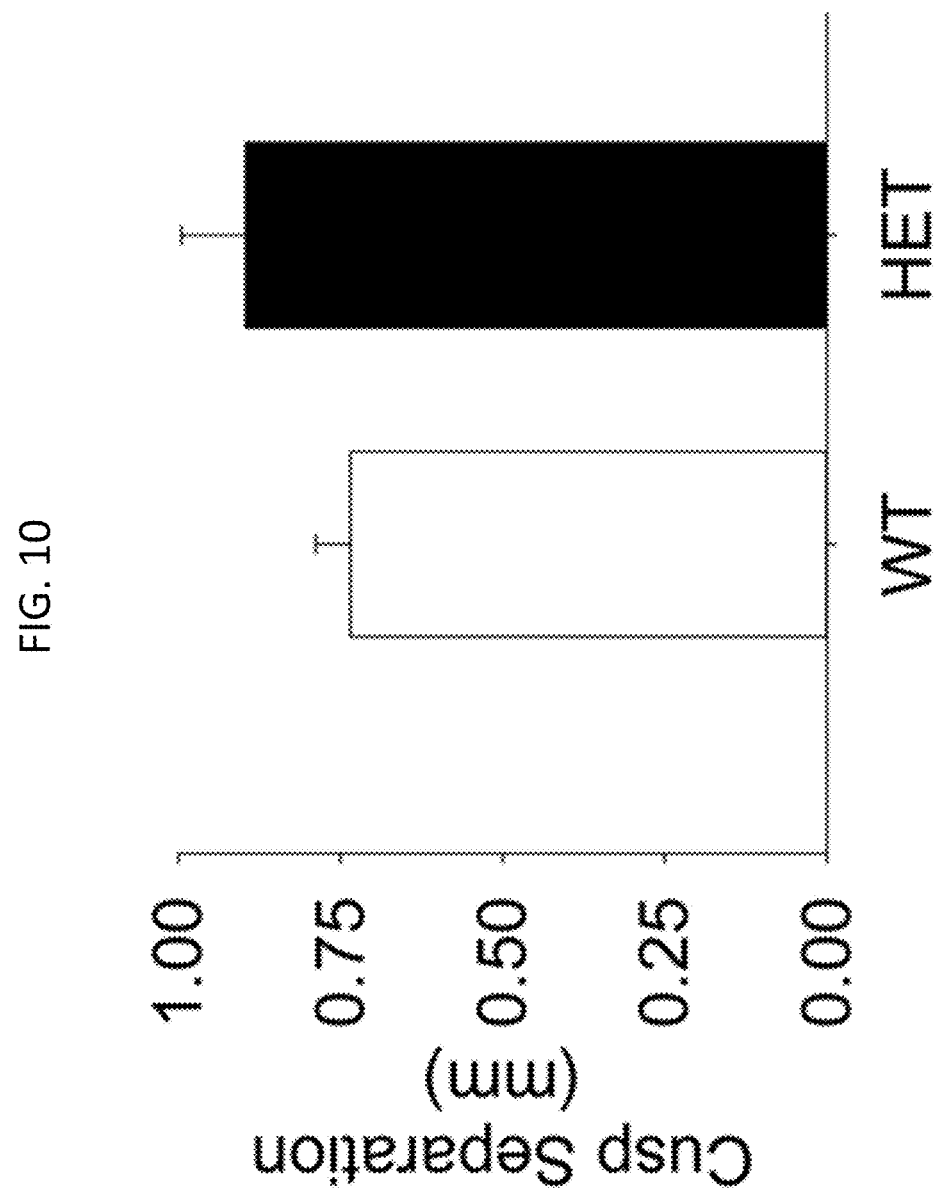
FIG. 10 is a graph plotting aortic valve function in mice deficient in one copy of DNMT3b. Aortic valve function was measured using high-resolution echocardiography, in which the distance between two valve cusps is measured during the systolic phase of the cardiac cycle. Increases in cusp separation distance indicated improved valve function.

Echocardiographic evaluation of aortic valve function: Echocardiographic evaluation of aortic valve function is conducted as described elsewhere (Miller et al. 2009, supra; Hinton et al., *Am J Physiol Heart Circ Physiol* 294:H2480-2488, 2008; Barrick et al., *Am J Physiol Heart Circ Physiol* 297:H65-75, 2009; and Miller et al., *Circ Res* 108:1392-1412, 2011). In brief, a Vevo 2200 small animal ultrasound unit is used to evaluate 1) cusp separation distance from M-mode images, 2) peak transvalvular blood velocity, and 3) color Doppler screening for evidence of aortic valve regurgitation. As shown in FIG. 10, cusp separation distance and peak velocity correlated well across a wide range of degrees of valvular dysfunction, but correlated poorly in the presence of aortic valve regurgitation. Short- and long-axis views of the left ventricle also are acquired to evaluate ventricular function (Berry et al., *J Cardiovasc Magn Reson* 11:27, 2009).

Immunohistochemical/Histological Evaluation of Tissues: Fluorescent immunohistochemical techniques are used on sections cut from OCT-embedded samples (Miller et al. 2010, supra; and Miller et al. 2009, supra). Images are acquired using a Zeiss 510 Meta confocal microscope at 40× and 63× levels of magnification, and are analyzed using ImageJ.

Quantitative Real-Time RT-PCR: Aortic valve cusps are dissected, and tissue is processed and stored using commercially available lysis buffer with β-mercaptoethanol (Miller et al., *Am J Physiol Heart Circ Physiol* 298:H1600-1607, 2010). Quantitative real-time RT-PCR studies confirming array-detected changes in gene expression are performed on a StepOne Plus instrument (Applied Biosystems).

Quantitative Micro-Computed Tomography (µCT): Aortic valves are scanned ex vivo using computed tomography scanning (MicroCT40; Scanco Medical) to evaluate calcium burden as described elsewhere (Fitzpatrick et al., *Endocrinology* 144:2214-2219, 2003).

Indexes of Systemic Inflammation: For markers of systemic oxidative stress and inflammation, plasma myeloperoxidase levels (Matsumoto et al., *Circulation* 121:759-767, 2010) and serum amyloid A levels (Subramanian et al., *Arterioscler Thromb Vasc Biol* 28:685-691, 2008), respectively, are measured.

Figure 11:
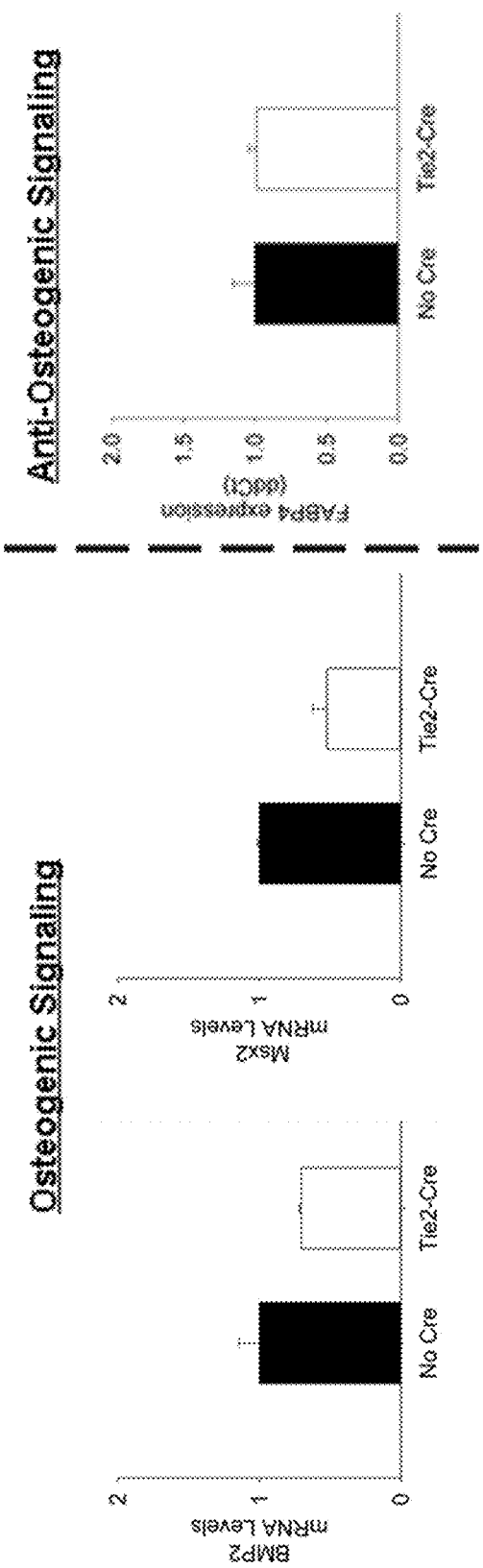
FIG. 11 is a series of graphs plotting transcriptional effects of reducing DNMT3b expression in aortic valve endothelial cells. DNMT3b conditional knockout mice ("foxed" mice) were crossed with mice expressing cre recombinase under the control of an endothelium-specific, Tie2 promoter. The mice were DNMT3b$^{FL/+}$ and did or did not carry the cre recombinase transgene. Endothelial DNMT3b haploinsufficiency reduced expression of BMP2 and Msx2 (left and center), but did not affect FABP4/PPARγ target gene expression (right).

These experiments demonstrated that deletion of one copy of DNMT3b in aortic valve endothelium reduced expression of the osteogenic molecules BMP2 and Msx2, but did not affect expression of PPARγ target genes (FABP4; FIG. 11). This observation was markedly different from what was observed when DNMT3b was selectively reduced in aortic valve interstitial cells.

Figure 12:
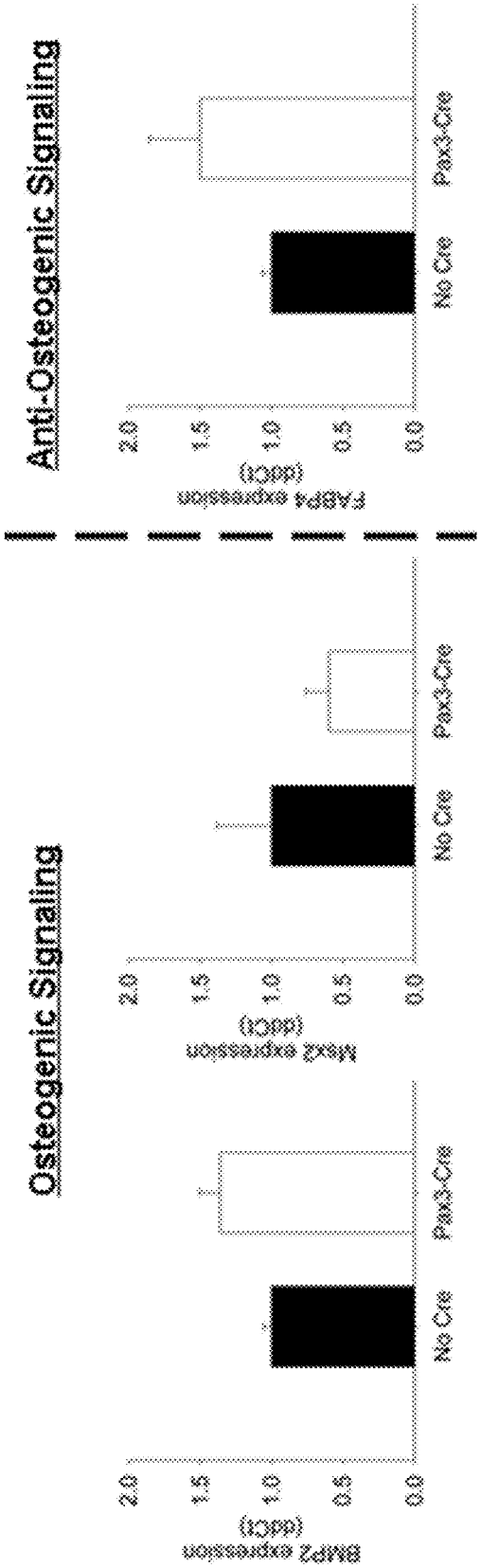
FIG. 12 is a series of graphs plotting transcriptional effects of reducing DNMT3b expression in aortic valve interstitial cells. DNMT3b conditional knockout mice ("foxed" mice) were crossed with mice expressing cre recombinase under the control of an interstitium-specific, Pax3 promoter. The mice were DNMT3b$^{FL/+}$ and did or did not carry the cre recombinase transgene. Interstitial cell DNMT3b deficiency did not reduce BMP2 expression (left), but reduced Msx2 expression (right). This may occur secondary to de-repression and hypomethylation of PPARγ target genes.

In addition, these experiments showed that deletion of DNMT3b in aortic valve interstitial cells in vivo (using Pax3-Cre$^+$/DNMT3b$^{FL/FL}$ mice, which express cre in neural crest-derived cells during development) was found to increase expression of FABP4 (an anti-osteogenic gene and target of PPARγ; FIG. 12). This finding was consistent with the hypothesis that DNMT3b represses anti-osteogenic genes in CAVD. Deletion of DNMT3b in aortic valve interstitial cells in vivo also reduced Msx2 expression (FIG. 12), consistent with repression of osteogenic signaling due to increases in PPARγ signaling. Unlike the effects of reducing DNMT3b in aortic valve endothelium, deletion of DNMT3b did not reduce BMP2 expression (FIG. 12), suggesting that DNMT3b is likely to have markedly different transcriptional effects on aortic valve endothelial and interstitial cells.

Example 4

Effects of DNMT3b Overexpression

Figure 13:
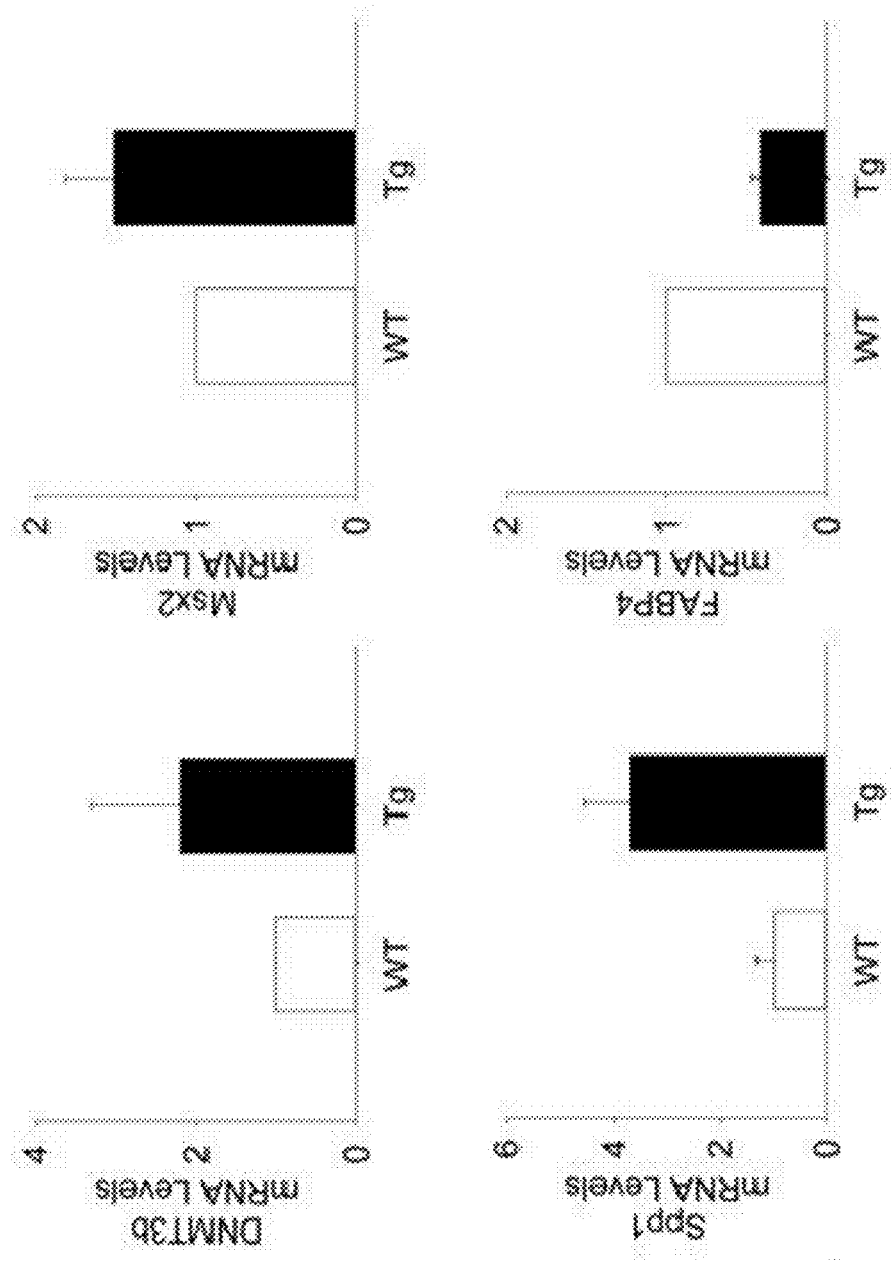
FIG. 13 is a series of graphs plotting levels of mRNA for osteogenic and anti-osteogenic genes in normocholesterolemic mice that overexpress DNMT3b. Conditional overexpression of DNMT3b (top left) by two-fold significantly increased expression of the pro-osteogenic gene Spp1 (bottom left) and significantly repressed expression of the anti-osteogenic gene FABP4 (bottom right).

Expression of DNMT3b was induced in young, normocholesterolemic mice containing a doxycycline-inducible DNMT3b transgene (The Jackson Laboratory, Bar Harbor, Me.; Stock #017983, Col1a1-tetO-Dnmt3b1::R26-M2rtTA). After seven days of continued conditional overexpression, mRNA levels for several osteogenic and anti-osteogenic genes were measured in aortic valve tissue. As shown in FIG. 13, DNMT3b overexpression led to increased osteogenic gene expression, and repressed anti-osteogenic gene expression. In particular, treatment of the transgenic mice with doxycyline (Tg conditions) resulted in upregulation of DNMT3b (top left panel) and the osteogenic genes Msx2 (top right panel) and SPP1 (bottom left panel). Of particular interest, the anti-osteogenic gene FABP4 was significantly downregulated (bottom right panel), suggesting that DNMT3b may serve to silence that protective pathway. Thus, even a two-fold induction of DNMT3b (compared to a 15-fold induction in human tissue) significantly increased pro-osteogenic gene expression (e.g., SPP1) and significantly repressed anti-osteogenic gene expression (FABP4).

Example 5

Effects of Inactivating One Copy of DNMT3b

Figure 14A:
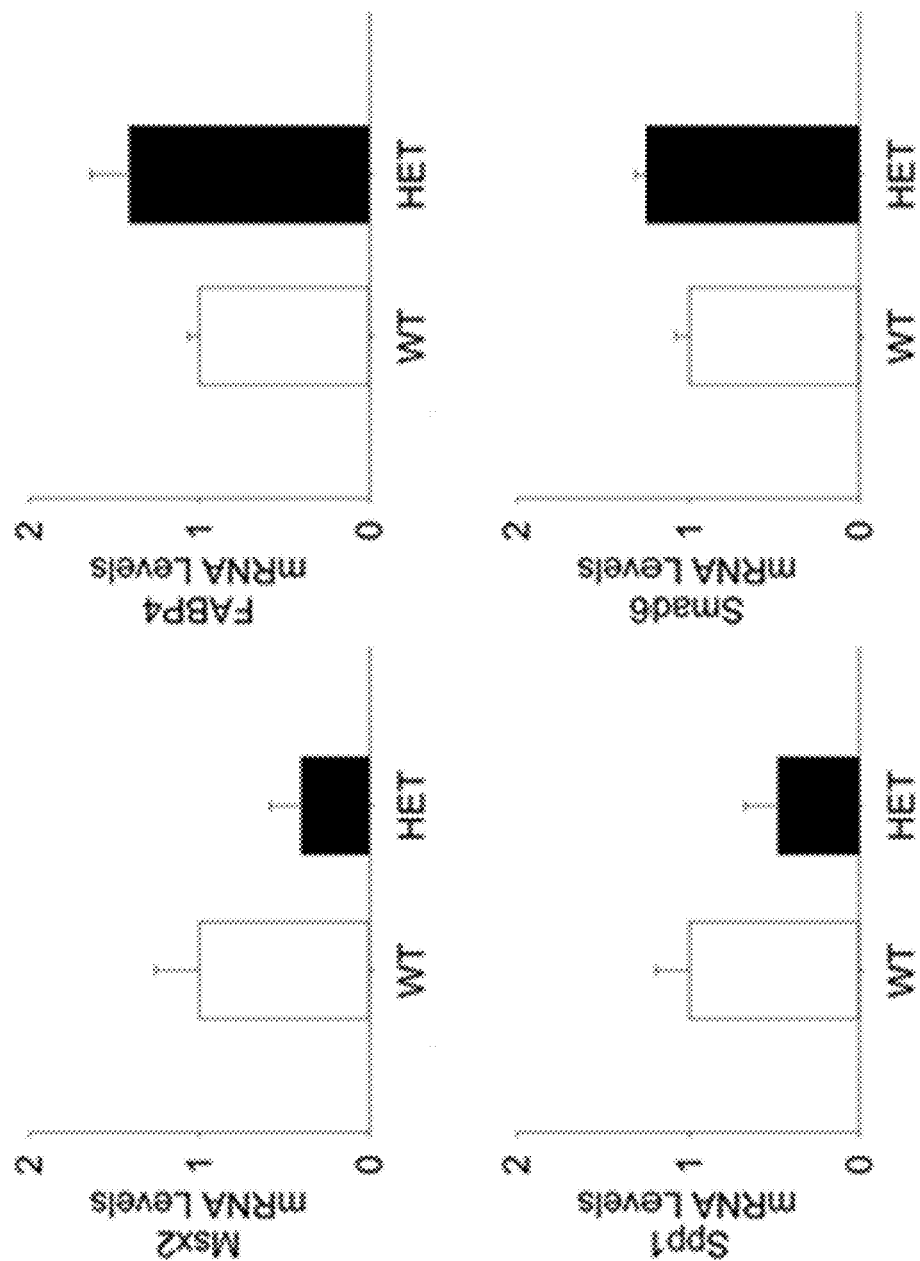

Hypercholesterolemic mice having one active and one inactivated DNMT3b gene were generated by crossing low density lipoprotein deficient/apolipoprotein B100-only mice (obtained from Dr. Stephen Young, UCLA) with DNMT3b-deficient mice having an inactivated catalytic domain (obtained from the Mutant Mouse Regional Resource Center (MMRRC;), stock number 029886-UNC). These animals were evaluated to determine the effect of haploinsufficiency on gene expression and CAVS progression. DNMT3b haploinsufficiency led to attenuation of osteogenic gene expression, as expression of the osteogenic molecules Msx2 and Spp1 was reduced (FIG. 14A, top left and bottom left, respectively), and increased anti-osteogenic gene expression, as expression of the anti-osteogenic molecules FABP4 (a PPARγ target) and Smad6 (a negative regulator of BMP signaling) was increased (FIG. 14B, top right and bottom right, respectively). In addition, DNMT3b haploinsufficiency was observed to slow progression of calcific aortic valve disease in a hypercholesterolemic mouse model of valvular stenosis (FIG. 14B).

Taken together, the above results indicate that 1) DNMT3b is dramatically elevated in valve tissue from humans with severe stenosis, 2) overexpression of DNMT3b significantly increases osteogenic signaling and reduces anti-osteogenic signaling in valves from genetically-altered mice, and 3) reducing DNMT3b levels by 50% in a mouse model of aortic valve stenosis significantly reduces osteogenic signaling, increases anti-osteogenic signaling, and slows progression of valvular stenosis. Collectively, these data strongly implicate DNMT3b in the pathogenesis of human aortic valve disease, show that experimentally increasing DNMT3b in vivo elicits molecular changes that are consistent with accelerated valve calcification, and demonstrate that reducing DNMT3b levels by a therapeutic amount (50% in haploinsufficient mice) significantly slows progression of valve disease even in the face of severe hypercholesterolemia. When combined with observations in multiple organ systems that reducing DNMT3b does not result in significant derangements in organ function, these data suggest that development of a novel DNMT3b inhibitor will slow valve calcification in humans and represent a breakthrough in the medical management of patients with aortic valve stenosis.

Figure 15:
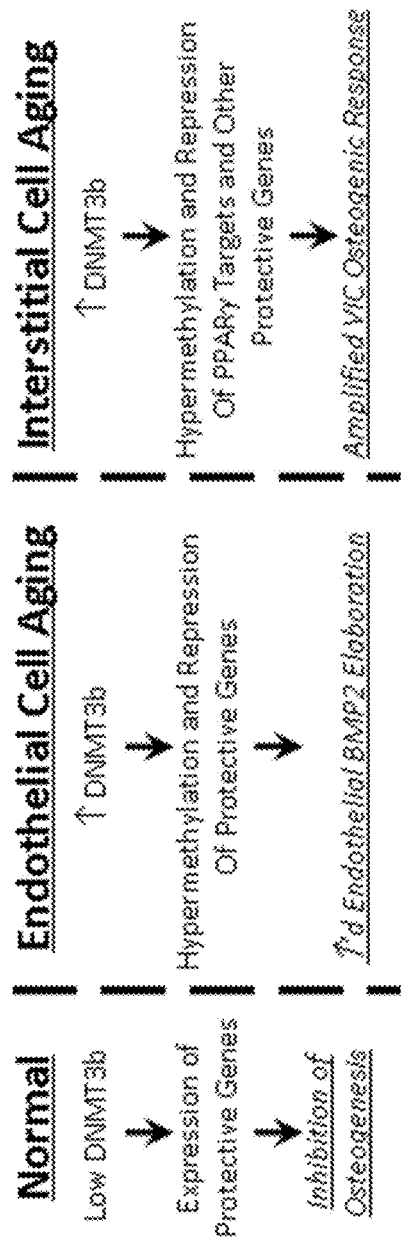
FIG. 15 is a diagram depicting possible patterns of methylation, gene expression, and osteogenic responses that may occur in normal aortic valve cells (left), or in aging endothelial (center) or interstitial (right) aortic valve cells.

A model for the patterns of methylation, gene expression, and osteogenic responses occurring in normal aortic valve cells vs. aging aortic valve cells is presented in FIG. 15. In particular, increases in DNMT3b in aging cells may lead to hypermethylation and repression of protective genes in endothelial and interstitial aortic valve cells, resulting in increased endothelial BMP2 levels, and an amplified osteogenic response in interstitial cells.

Figure 16:
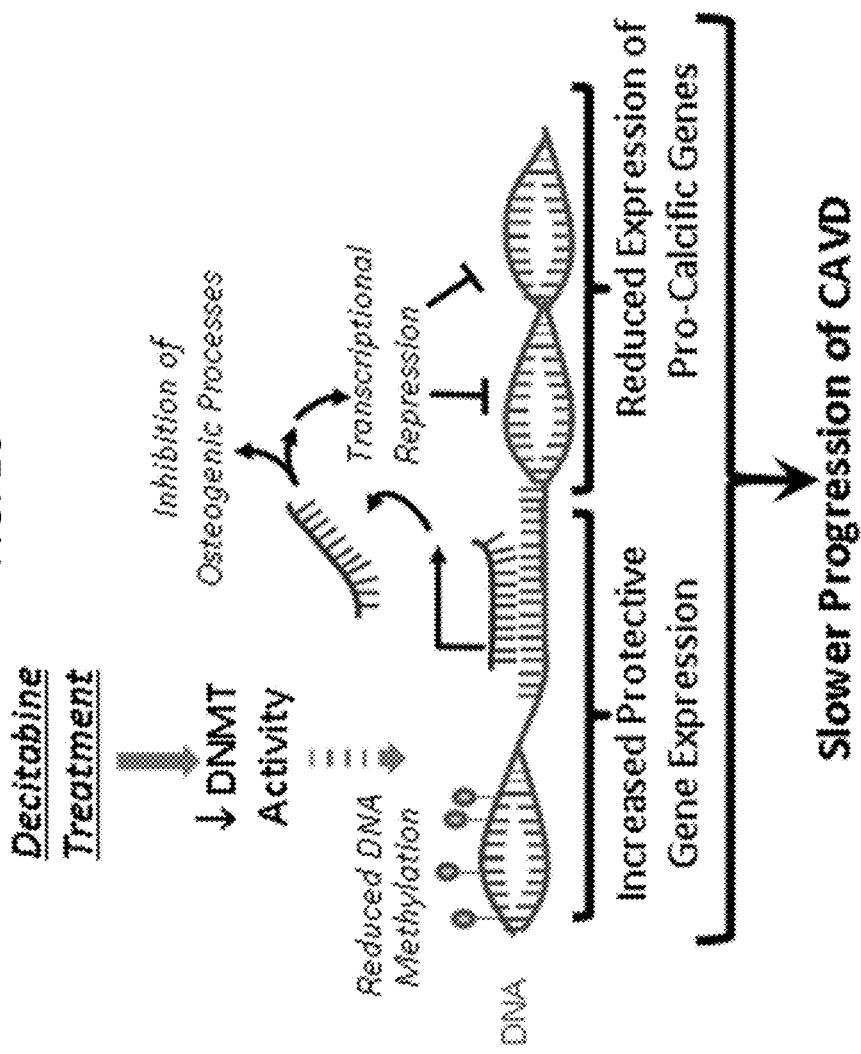
FIG. 16 is a diagram depicting a model for the mechanism by which a DNMT inhibitor such as Decitabine slows progression of CAVD.

FIG. 16 depicts a model of the mechanism through which a DNMT such as Decitabine may slow the progression of CAVD. As indicated, the reduced level of DNA methylation may permit increased expression of protective genes, which subsequently inhibit osteogenic processes and repress expression of pro-calcific genes.

Example 6

Statistical Analysis for High Throughput Analysis of DNA Methylation and Gene Expression Normalization of Microarray Data: The Affymetrix gene expression data are normalized using quantile normalization and then summarized into a single value per probe-set using Tukey's median polish. All analyses are performed on the log-2 scale, using R and the R-package "rma" (R Core Team, *R: A language and environment for statistical computing*, R Foundation for Statistical Computing, 2007; and Irizarry et al., *Biostatistics* 4:249-264, 2003), available from Bioconductor (Gentleman et al., *Genome Biol* 5:R80, 2004).

Differential gene expression analysis: The analysis is based on a total of 54,676 transcripts. Differential expression analysis is carried out using the Limma linear modeling package available in the R Bioconductor software suite (Smyth, *Stat Appl Genet Mol Biol* 3:Article 3, 2004). In this approach, a linear model is fit for all genes with respect to normal and stenotic tissue (or control and intervention groups), allowing for genes to be tested for differential expression. To control the false discovery rate, P-values are adjusted for multiple comparisons using the Benjamini and Hochberg method (Benjamini and Hochberg, *J Roy Stat Soc B* 57:289-300, 1995).

Infinium 450K DNA Methylation Analysis: DNA methylation is determined by the percent methylation per CpG site, i.e., the ratio of fluorescent signal from the methylated allele to the sum of the fluorescent signal from both methylated and unmethylated alleles (Sandoval et al., supra). These percent methylation values range from 0 (unmethylated) to 1 (methylated). The presence and nature of systematic biases are assessed for the methylated, unmethylated, and percent methylation signals via residual MVA plots. The methylated and non-methylated signals are likely to be differentially expressed for a large number of the sites assayed. The proper normalization strategy is investigated, either within methylated and unmethylated signals via two-color normalization algorithms, or on the percent methylation signals via single channel normalization algorithms (Eckel et al., *Bioinformatics* 21:1078-1083, 2005; and Ballman et al., *Bioinformatics* 20:2778-2786, 2004). Both of these algorithms are similar to cyclic loess, but are computationally faster and allow explicit modeling of design information (Dudoit et al., *Statistica Sinica* 12:111-139, 2002). As wholesale changes in methylation status across time points are not expected, all time points are normalized together. These assays typically have small linear biases and virtually no non-linear biases. Differential expression and regression modeling are performed via linear mixed effects models and the pertinent contrasts, adjusting for covariates as needed.

Example 7

Statistical Analysis for In Vivo and Low Throughput Studies

Data from in vivo studies are analyzed using a two-way ANOVA (age×genotype). Post-hoc testing is performed using Tukey's HSD method. Based on previous studies (Miller et al. 2010a, supra; Miller et al. 2009, supra; and Miller et al., *J Am Coll Cardiol* 52:843-850, 2008) and preliminary data, with power >0.90 when α=0.05, it is anticipated that these studies require (1) 20 animals per group to detect a 10% change in valve function (which does not require sacrificing animals), (2) 10 animals per group to detect a 25% change in gene expression, (3) 15 animals per group to detect a 20% change in valve calcification with μCT, (4) 10 animals per group to detect a 20% change in immunohistochemical parameters, and (5) 15 animals per group to detect a 20% change in DNA methylation with pyrosequencing. Thus, 80 animals per group/time point are used for each study.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing calcific aortic valve stenosis (CAVS) in a patient, comprising administering to a patient identified as having CAVS a therapeutically effective amount of a DNA methyltransferase (DNMT) inhibitor, wherein said CAVS is reduced, and wherein the DNMT inhibitor is an inhibitor of DNA methyltransferase 3b (DNMT3b).

2. The method of claim 1, wherein the DNMT inhibitor further is an inhibitor of DNA methyltransferase 1 (DNMT1).

3. The method of claim 1, wherein the DNMT inhibitor further is an inhibitor of DNA methyltransferase 3a (DNMT3a).

4. The method of claim 1, wherein the DNMT inhibitor is 5-aza-2'-deoxycytidine.

5. The method of claim 1, wherein the patient is a human.

* * * * *